United States Patent [19]

Mullins et al.

[11] Patent Number: 5,264,520

[45] Date of Patent: Nov. 23, 1993

[54] POLYMERIZATION OF CYCLIC POLY(ARYL ETHER) OLIGOMERS

[75] Inventors: Michael J. Mullins; Edmund P. Woo, both of Midland, Mich.

[73] Assignee: The Dow Chemical Company, Midland, Mich.

[21] Appl. No.: 547,658

[22] Filed: Jul. 3, 1990

Related U.S. Application Data

[63] Continuation-in-part of Ser. No. 402,177, Sep. 1, 1989, abandoned.

[51] Int. Cl.$^5$ .................. C08G 8/02; C08G 14/00
[52] U.S. Cl. ............................ 528/125; 528/86; 528/126; 528/128; 528/170; 528/172; 528/174; 528/190; 528/211; 528/216; 528/220; 528/226; 528/228
[58] Field of Search .......... 528/86, 125, 126, 128, 528/170, 174, 172, 190, 211, 216, 220, 226, 228, 377

[56] References Cited

U.S. PATENT DOCUMENTS

| | | | |
|---|---|---|---|
| 4,136,087 | 1/1979 | Williams, III et al. | 528/79 |
| 4,740,583 | 4/1988 | Brunelle et al. | 528/370 |
| 4,794,155 | 12/1988 | Woo et al. | 528/125 |
| 4,851,455 | 7/1989 | Job et al. | 525/132 |
| 4,880,884 | 11/1989 | Mullins et al. | 525/549 |
| 5,110,893 | 5/1992 | Fukuyama | 528/125 |

FOREIGN PATENT DOCUMENTS

| | | | |
|---|---|---|---|
| 0317226 | 5/1989 | European Pat. Off. | 549/10 |
| 1226882 | 9/1989 | United Kingdom | 549/11 |

OTHER PUBLICATIONS

Cella, et al., Ring Opening Polymerization of Cyclic Ethers & Thioethers, Imides, Sulfones via Aromatic Ether-Ether Exchange; Amer. Chem. Soc. Polymer Prep. vol. 30, No. 2 (1989), pp. 142-143.
Cella, et al., Poly. Prepr. 30(2), 581 ∝ 582, (Sep. 1989).

*Primary Examiner*—John Kight, III
*Assistant Examiner*—P. Hampton-Hightower

[57] ABSTRACT

This invention is a process for the preparation of poly(aryl ethers) from cyclic poly(aryl ether) oligomers. These low melt viscosity cyclic oligomers undergo ring opening and chain extension upon heating in the presence of a catalyst, forming high molecular weight linear polymers with no coproduct formation. Finished thermoplastic parts and composites may be prepared using this technology with processing techniques normally restricted to thermosetting monomers.

63 Claims, No Drawings

POLYMERIZATION OF CYCLIC POLY(ARYL ETHER) OLIGOMERS

This application is a continuation-in-part of application Ser. No. 07/402,177 filed Sep., 1989, hereby incorporated by reference, now abandoned.

BACKGROUND OF THE INVENTION

1. Field of the Invention

This invention relates to the polymerization of cyclic poly(aryl ether) oligomers. More particularly, this invention relates to methods for the preparation of poly(aryl ethers) from cyclic poly(aryl ether) oligomers, and especially to the preparation therefrom of composites containing reinforcing materials through ring opening polymerizations.

Low melt viscosity cyclic oligomers may be catalytically converted to high molecular weight poly(aryl ethers) which are noted for high temperature stability and solvent resistance. These cyclic oligomers are useful for preparing shaped articles where the high melt viscosities typical of high molecular weight linear poly(aryl ethers) are undesirable.

The use of thermoplastic resins to prepare composites has received considerable attention in recent years. An important advantage of thermoplastic composites relative to those based on thermosets is excellent retention of mechanical properties after impact.

An important disadvantage of thermoplastic composites is the cost of manufacture of small numbers of finished parts. Molds and autoclaves suitable for the high temperature and pressure required are expensive. In addition, the high melt viscosity of thermoplastics causes considerable difficulties in the coating of fibers without the formation of voids, which are detrimental to the mechanical properties of the composite.

One solution to this problem is to prepare a cyclic precursor which ring opens upon heating. Ring opening polymerizations are desirable for this application in that there are no coproducts which must be removed.

2. Description of Related Art

An example well known in the art of the use of a cyclic precursor which ring opens upon heating in the presence of a catalyst is that of caprolactam. In this application caprolactam is used as a low viscosity monomer for the preparation of nylon 6, an aliphatic polyamide. A second example, described by Burnelle, et al., in U.S. Pat No. 4,644,053 (1987) is the polymerization of cyclic carbonates of Bisphenol A, (2,2'-bis(4-hydroxyphenyl)propane).

A consideration for many composite applications is that they need resistance to high temperatures, humid environments, and chemicals such as fuels, hydraulic fluids, and cleaning solvents. The aforementioned aliphatic polyamide and Bisphenol A polycarbonate do not have the necessary combination of properties. Poly(aryl ethers) are an important class of thermoplastic resins employed for the manufacture of composites which do meet the above requirements. Therefore, low viscosity precursors to poly(aryl ether) thermoplastics are highly desirable for the manufacture of composites. The Applicants have developed a general method and several specific methods for the preparation of cyclic poly aryl ether) oligomers, which are described in the Applicant's copending application titled "Cyclic Poly(Aryl Ether) Oligomers", which is hereby incorporated by reference.

There are numerous examples in the prior art of the preparation of poly (aryl ethers) and related polymers, usually with the aid of a polymerization catalyst such as an alkali metal halide or carbonate, including U.S. Pat. No.'s 3,441,538, 3,941,748, 4,169,178, 4,320,224, 4,638,044, 4,687,833, 4,731,429, 4,748,227, and 4,767,838. In U.S. Pat. No. 4,360,630, this type of polymer was used to prepare composites. EP 317,226 discloses macrocyclic compounds, including cyclic ethers, containing polyarylene units and other cyclic units, and the polymerization thereof. WO 88/06605 discloses random macrocyclic monomer and oligomer compounds containing a spiro(bis)indane moiety.

SUMMARY OF THE INVENTION

The present invention relates to a process for the preparation of high molecular weight poly(aryl ethers) which comprises subjecting a polymerizable composition comprising at least one cyclic poly(aryl ether) oligomer represented by the formula

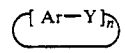

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom, to ring opening polymerization conditions. The polymerizable composition can contain a single cyclic oligomer, a mixture of oligomers having differing degrees of polymerization but the same repeating unit, or a mixture of oligomers with differing repeating units and differing degrees of polymerization.

Another aspect of the present invention relates to a process for the preparation of a composite which comprises subjecting a polymerizable composite composition comprising a reinforcing material and at least one cyclic poly(aryl ether) oligomer represented by the formula

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom, to ring opening polymerization conditions.

A variety of metal salts can function as the ring opening polymerization catalyst, with cesium fluoride being an especially preferred ring opening polymerization catalyst. The catalyst can be produced in situ in the polymerizable composition, desirably from the reaction of a dihalogenobenzenoid compound and a metal salt of a bisphenol. The polymerization process can be carried out in a mold to produced a finished article from the high molecular weight polymer so produced, with no undesirable side products which would otherwise have to be removed.

Further, reinforcing materials can be incorporated into the polymerizable composition of one or more cyclic oligomers and the ring opening catalyst to form a composite. The polymerizable composition which contains a cyclic oligomer has a low viscosity, and it has an especially low viscosity when it contains a mixture of oligomers. Therefore, the composition is very effective in coating the reinforcing fibers without the formation of voids. Void formation results in undesirable mechanical properties in the finished composite article, and especially in reduced strength. Void formation has been a problem with prior art methods of composite preparation which employ high molecular weight polymers with high melt viscosities.

DESCRIPTION OF THE PREFERRED EMBODIMENTS

The general objective of this invention is to prepare novel cyclic poly(aryl ether) oligomers, which are characterized by low melt viscosities, and which are then used for ring opening polymerizations. Each mention of the term ether should be understood to include thioether as well. These cyclic poly(aryl ether) oligomers contain (Ar—Y) repeating units and are represented by the formula

where each Y is divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 or 2 all linkages between independent aromatic rings comprise at least one atom.

The aromatic diradical may be quite simple, consisting of a single arylene group with only one aromatic ring, and one electron withdrawing group attached to the aromatic ring. In other embodiments the aromatic diradical is more complex and may contain more than one arylene group. The arylene groups contain from 6 to 20 carbon atoms and one or more aromatic rings.

The electron withdrawing group in one embodiment is monovalent, and, thus, pendant from an aromatic ring. In another embodiment the electron withdrawing group is divalent and in the backbone of the ring. In further more complex embodiments of the present invention the divalent electron withdrawing groups comprise various combinations of electronegative groups and arylene groups.

The aromatic diradical may also contain one or more linking groups in the backbone of the ring which are heterocycles or groups of heterocycles.

The cyclic poly(aryl ether) oligomers of the present invention are prepared by the addition of the reactants as solutions to a reaction medium that dilutes and disperses the reactants. Reaction times as long as ten days have been used, but in most cases the cyclization reactions is favorable enough that a point of diminishing returns is reached in a much shorter time, often within one day or less.

A variety of starting materials and different reactions can be used in this general method of preparation. Under the reaction conditions of the general method of preparation of the present invention the lifetimes of any intermediates formed is short, with ring closure being favored. The ultimate yield of cyclic poly(aryl ether) oligomers is high.

These cyclic poly(aryl ether) oligomers can be prepared by several specific novel methods which are modifications of the methods described in the prior art which are used to prepare high molecular weight linear polymers. Whereas the prior art preparative methods are generally characterized by batchwise addition of the various reactants and high reactant concentrations, the preparative methods of the present invention are characterized by gradual addition of the reactants over a period of time. The reaction conditions are such that when the reactants are brought into contact ring-forming intermediates are immediately produced.

These conditions provide an environment in which any reactive intermediate preferably undergoes ring closure at a relatively low degree of polymerization, with n no more than about 20, more preferably no more than about 10, rather than continuing polymerization linearly to form a high molecular weight polymer. In cases where the synthetic procedure results in an intermediate which itself is a relatively long structure, ring closure may be favored for a single unit, with the result that n is 1. It should be understood that the term "oligomer" is meant to include these cases where n is 1, or where there is a mixture of oligomers with different n values including n equal to 1.

The cyclic poly(aryl ether) oligomers prepared in this fashion can then be isolated either as a mixture of oligomers or separated into individual oligomers. For some starting materials and methods of preparation under appropriate reaction conditions, a single oligomer may predominate as the reaction product. These products have superior characteristics for the production of composites and coatings.

These low melt viscosity cyclic poly(aryl ether) oligomers may be catalytically converted to high molecular weight poly(aryl ethers) which are noted for high temperature stability and solvent resistance. These cyclic oligomers are useful for preparing shaped articles where the high melt viscosities typical of high molecular weight linear poly(aryl ethers) are undesirable.

When polymerized these cyclic oligomers are useful also for the preparation of protective coatings and adhesives, and for various electronics applications, such as passivation.

The methods of this invention may be used to polymerize cyclic poly(aryl ether) oligomers to form high molecular weight polymers which are substantially identical to those present in various commercial products. These commercial products are prepared by prior art methods in which low molecular weight starting materials react to produce high molecular weight linear products. Some examples are ICI's Victrex® PES (polyether sulfone), Amoco's Udel® and Radel® polysulfone, GE's Ultem® polyetherimide, ICI's Victrex® PEEK (poly ether ether ketone) and BASF's Ultrapek® polyetherketone.

The aromatic diradical Ar has at least one electron withdrawing group attached to an aromatic ring. Some suitable monovalent groups are —CN, —NO$_2$, —CHO, —CO$_2$R, —CO$_2$NH$_2$, —P(O)(OR)$_2$, —P(O)R$_2$, —$^+$PR$_3$, —$^+$NR$_3$, —$^+$SR$_2$, —F and —CF$_3$.

In another aspect of the present invention the electron withdrawing group is divalent and in the backbone of the ring. In a preferred embodiment the divalent electron withdrawing group comprises an electronegative group Z which is —SO$_2$—, —CO—, —CONH—, —CONR—, —$^+$NR$_2$—, —$^+$PR$_2$—, —$^+$SR—, —P(O)R—, —C$_6$F$_4$—, —C$_6$F$_4$C$_6$F$_4$—, —C(CF$_3$)$_2$—, —CHCH—, —N=N—, —CHNNCH—, where R is a hydrocarbyl radical of 1 to 12 carbon atoms, imidazole, oxazole, pyrazole, isoxazole or oxapyrazole, and the cyclic poly(aryl ether) oligomer is represented by the formula

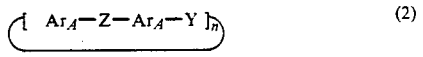 (2)

where Y and n are as previously defined and each Ar$_A$ is an arylene group containing at least one aromatic ring.

The arylene group Ar$_A$ contains from 6 to 20 carbon atoms and one or more aromatic rings, through which it is incorporated into the ring of the oligomer. In more complex arylene groups independent aromatic rings are linked by divalent linking groups such as —O—, —S—, Z as defined above, and simple hydrocarbyl groups. For oligomers with values of n equal to 1 or 2 all linkages between independent aromatic rings comprise at least one atom, but for others it may be a direct bond. Some preferred arylene groups are phenylene and substituted phenylene, and the following complex arylene groups:

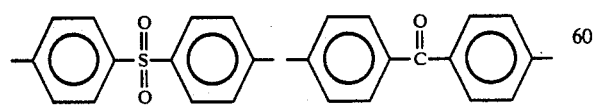

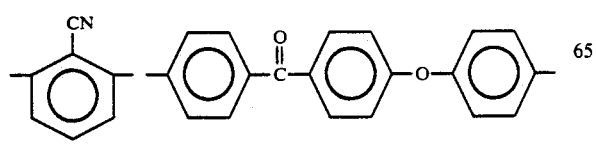

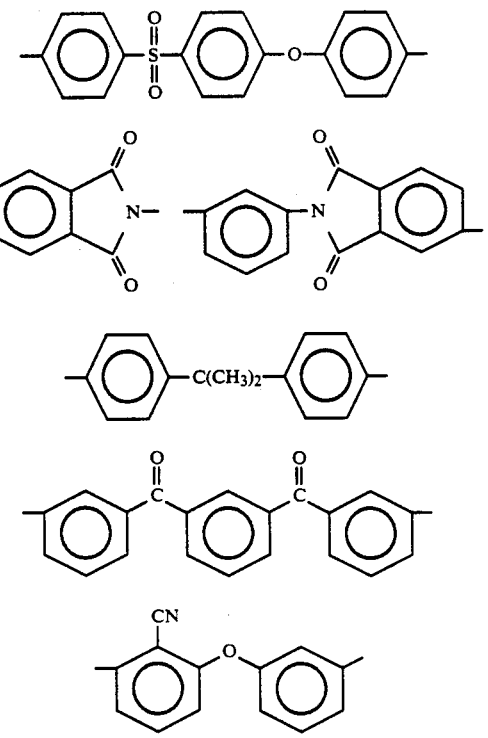

In other embodiments the electron withdrawing group attached to Ar may comprise several independently selectable Z groups and several independently selectable Ar$_A$ groups.

The aromatic diradical may additionally contain one or more linking groups L in the backbone of ring where preferred examples of suitable linking groups include the following:

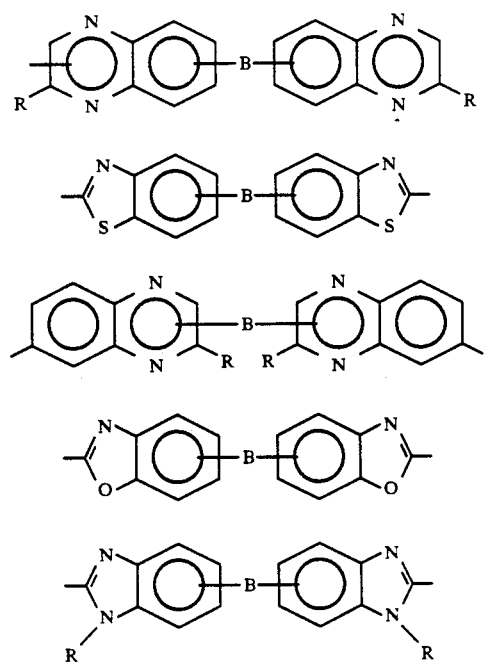

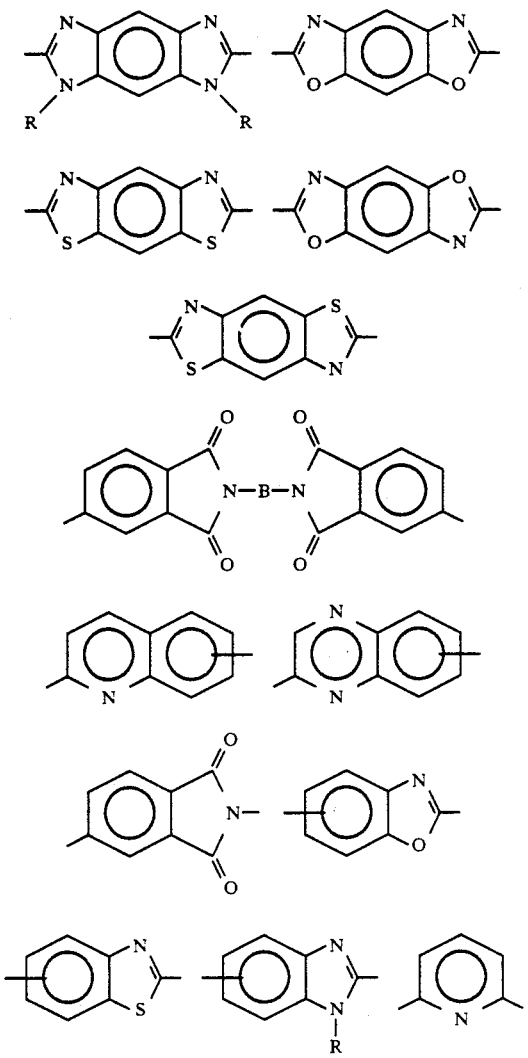

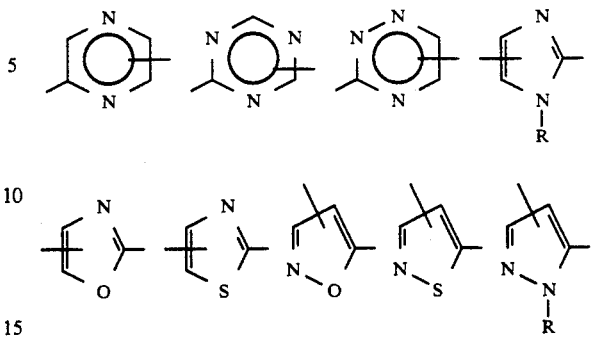

where R is a $C_1$ to $C_{12}$ hydrocarbyl radical and each of the heterocycles may be additionally substituted with one or more $C_1$ to $C_{12}$ hydrocarbyl radical, halogens, $C_1$ to $C_{12}$ alkoxy or aryloxy radicals, cyano, nitro, alkylcarbonyl, formyl, alkoxycarbonyl or aryloxycarbonyl, arylsulfonyl: B is in each occurrence a direct bond, —O—, —S—, —SO$_2$—, a carbonyl, a phosphinyl, a phosphine oxidyl, a tertiary aminyl, and a $C_1$ to $C_{24}$ hydrocarbyl radical optionally substituted with halogens, $C_1$ to $C_{12}$ alkoxy or aryloxy radicals, cyano, nitro, alkylcarbonyl, formyl, alkoxycarbonyl or aryloxycarbonyl, arylsulfonyl, or carbonylarylcarbonyl.

In many cases a desirable embodiment of the present invention is a composition comprising a mixture of cyclic poly(aryl ether) oligomers as represented by formula (1), which encompass the specific subgroups discussed up to now. A preferred embodiment is such a composition wherein the cyclic poly(aryl ether) oligomers of the mixture are represented by one or more of formulas I-XI

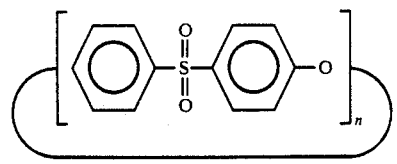

I

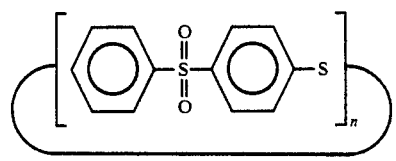

II

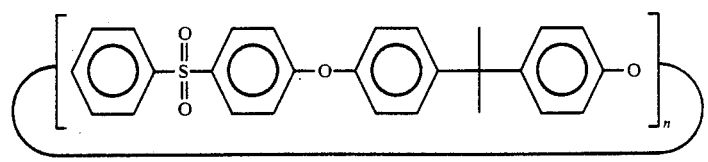

III

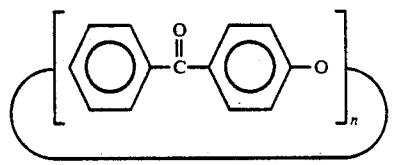 IV
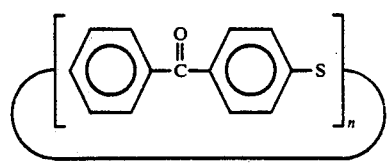 V
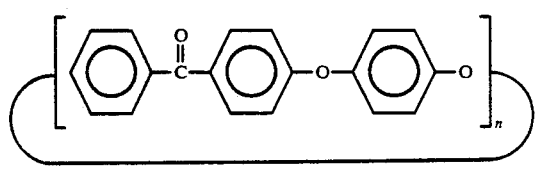 VI
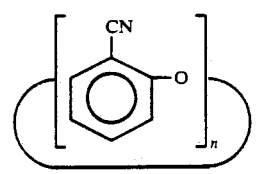 VII
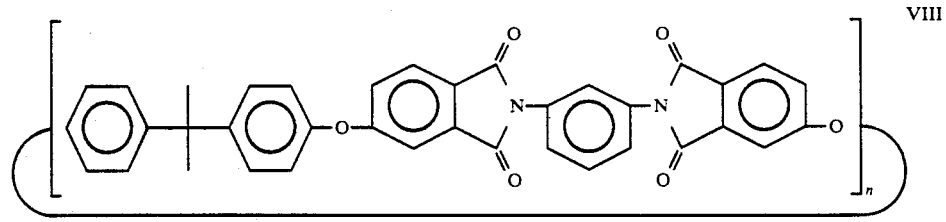 VIII
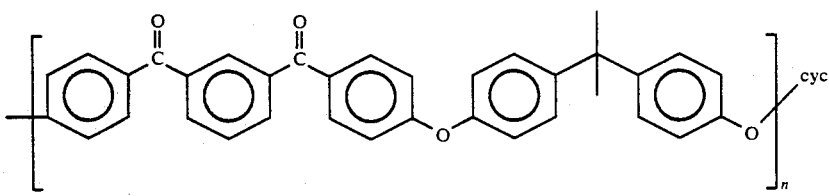 IX
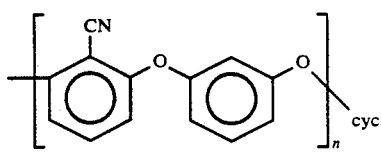 X
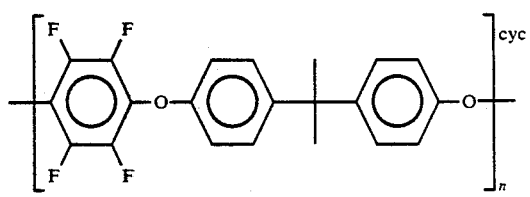 XI
The term "cyc" in association with a structure indicates a cyclic structure.

is an abreviation used in a structural formulas to conveniently represent —C(CH$_3$)$_2$—, as in a bisphenol A nucleus.

Especially preferred embodiments are those wherein the cyclic poly(aryl ether) oligomers of said mixture are represented by

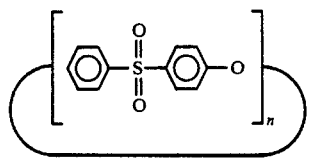

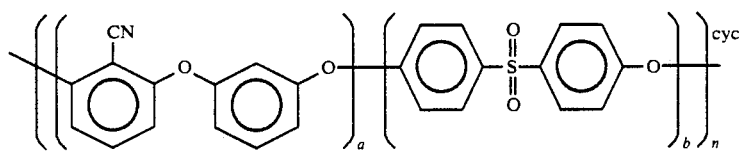

or

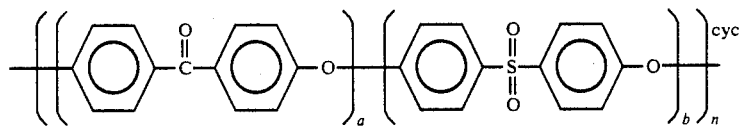

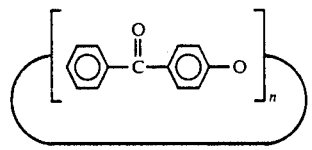

IX

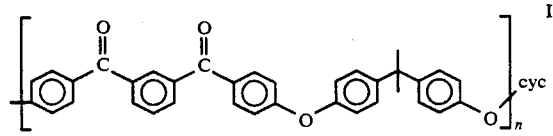

X

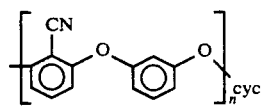

or

XI

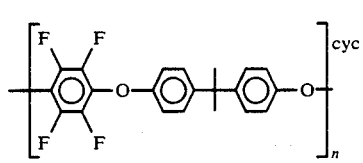

An example of a more complex embodiment of the present invention is that represented by the formula

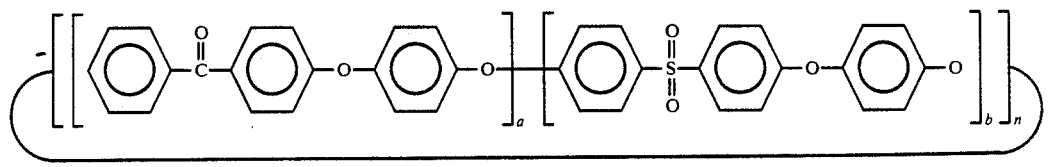  (3)

where Z, Y and n are as previously defined: Y$_1$ is divalent oxygen or divalent sulfur independently selectable from Y; Ar$_1$, Ar$_2$, Ar$_3$ and Ar$_4$ are arylene groups independently selected from the group consisting of Ar$_A$; Z$_1$ is independently selectable from the group consisting of Z; and a and b are integers of from 1 to 3. In formula 3 a and b indicate the ratio of the blocks and are not meant to be indicated of any ordering of blocks in this embodiment.

Preferred embodiments which correspond to formula (3) are

Another embodiment is that of a composition comprising a mixture of oligomers corresponding to formula (3), including the specific example given above, either alone or in admixture with some other cyclic poly(aryl ether) oligomer.

Another complex embodiment corresponds to formula (4)

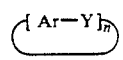  (4)

where Y, n, Z, Ar$_A$, and L are as previously defined.

Still another embodiment of the present invention is a composition which comprises a mixture of at least 10% of one or more cyclic poly(aryl ether) oligomers represented by the formula:

$$( Ar - Y )_n$$

and up to 90% of one or more linear poly(aryl ether) polymers wherein the repeating unit is:

$+Ar-Y+_m$ where Ar, Y and n are as previously defined, and m is an integer greater than 20. Admixture of the low melt viscosity oligomers of the present invention with high melt viscosity linear polymers lowers the viscosity of the composition so formed which is desirable in many applications.

Many of the methods described in the prior art for the production of high molecular weight poly(aryl ethers) can be modified according to the principles of the present invention and used to produce cyclic poly(aryl ether) oligomers. In particular, three methods will be described for producing these materials. In the first method an activated aryl dihalide is reacted with an aromatic diol in the presence of a base. An activated aryl dihalide as used herein is defined as an aryl dihalide which has attached to the aromatic ring at least one electron withdrawing group other than the two halide leaving groups. The prior art is replete with discussions concerning activated aryl dihalides. Examples of preferred activated aryl dihalides include 4,4'-difluorobenzophenone, 4,4'-dichlorobenzophenone, 4,4'-dinitrobenzophenone, bis-(4-fluorophenyl)sulfone, bis-(4-chlorophenyl)sulfone, bis-(4-chloro-3-nitrophenyl)sulfone, 4,4'-dichloroazobenzene, 4,4'-dichloroazoxybenzene, 1,3-bis-(4-fluorobenzoyl)benzene, 1,4-bis-(4-fluorobenzoyl)benzene, 1,3-bis-(4-chlorobenzoyl) benzene, 1,4-bis-(4-chlorobenzoyl)benzene, 2,6-difluorobenzenenitrile, 2,4-difluorobenzenenitrile, 2,6-dichlorobenzenenitrile, 2,4-dichlorobenzenenitrile, and hexafluorobenzene.

Examples of preferred diols include 1,2-ethanediol, 1,2-propanediol, 1,3-propanediol, 1,4-butanediol, 1,4-cyclohexanediol, 1,4-bis-(hydroxymethyl)benzene, 1,3-dihydroxybenzene, 1,4-dihydroxybenzene, 1,4-dihydroxy-2-methylbenzene, 1,6-dihydroxynaphthalene, 2,6-dihydroxynapthalene, bis-(4-hydroxyphenyl)-phenyl-methane, bis-(4-hydroxyphenyl)-diphenylmethane, 1,1-bis-(4-hydroxyphenyl)ethane, 1,2-bis-(4-hydroxyphenyl)ethane, 2,2'-bis-(4-hydroxyphenyl)propane, 1,1,1,3,3,3-hexafluoro-2,2'-bis-(4-hydroxyphenyl) propane, 1,1-bis-(4-hydroxyphenyl)-acetonitrile, 1,3-bis-(4-hydroxybenzoyl)benzene, 1,4-bis-(4-hydroxybenzoyl)-benzene, bis-(4-hydroxyphenyl)methane, bis-(4hydroxyphenyl)sulfone, bis-4-hydroxyphenyl)sulfide, bis-(4-hydroxyphenyl)ether, 4,4'-dihydroxybenzophenone, 4,4'-dihydroxybiphenyl, 4,4'-dihydroxyazobenzene, 4,4'-dihydroxyazoxybenzene, bis-(4-mercaptophenyl)ether, bis-(4-mercaptophenyl)sulfide, 3-mercaptophenol, 4-mercaptophenol, 1,3-dimercaptobenzene, 1,4-bis-(4-hydroxycumenyl)benzene and 1,4-dimercaptobenzene.

The second method for the preparation of cyclic poly(aryl ether) oligomers is similar to the first method except that no aromatic diol is used.

In any of the methods for preparation of cyclic poly(aryl ether) oligomers of the present invention where the basic role of the dihalide in the reaction is that of providing a halide leaving group, that role can be performed with compounds containing other leaving groups. The dinitro compounds corresponding to the mentioned dihalides are especially suitable as reactants in these methods. Therefore, although the discussion has been centered around dihalides and the other halide containing reactants, it should be understood that analogous reactants with other leaving groups, especially dinitro compounds, can be used.

Both methods ultimately lead to the same reactive intermediate, which is a linear oligomer capped with a halide at one end and a metal phenate at the other. In actual practice both of these methods are single step procedures.

Schemes I, II and III, below, schematically show these two methods, labeled as Method A and Method B, for three types of starting materials leading to the indicated reactive intermediates which then immediately go on to form the cyclic poly(aryl ether) oligomer products.

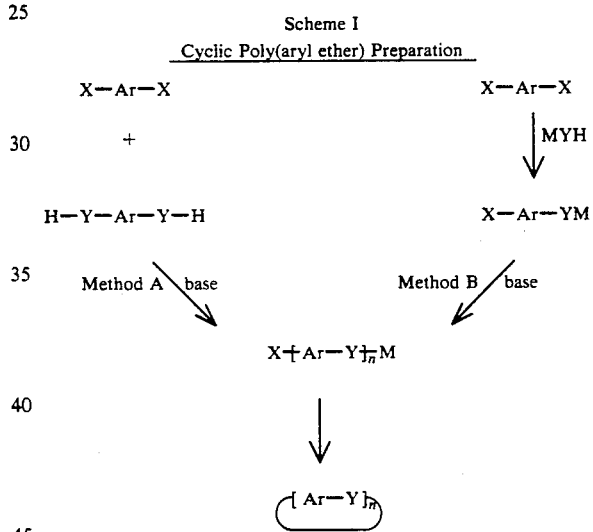

where Ar and Y are as previously defined, X is halide, X—Ar—X is an activated aryl dihalide, H—Y—Ar—Y—H is an aromatic diol or thiol, MYH is a base containing a metal M, X—Ar—YM is the mono salt produced by initial reaction of an activated aryl dihalide and the base, $X+Ar-Y+_n M$ is the intermediate linear oligomer capped with a halide at one end and a metal phenate at the other, n is from 1 to about 20, and

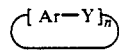

is the cyclic poly(aryl ether) oligomer.

Scheme II
Cyclic Poly(aryl ether) Preparation

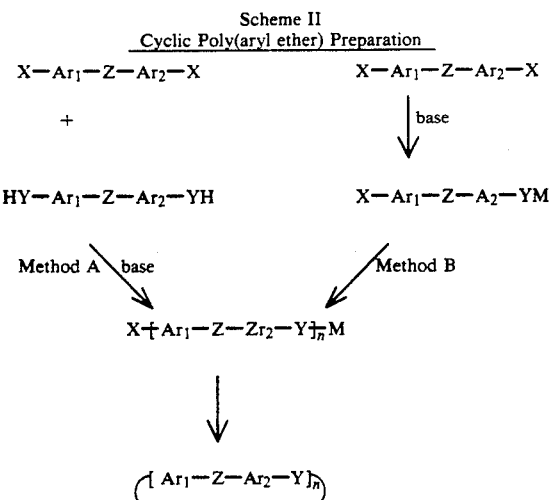

where $Ar_1$, $Ar_2$, Z, X, Y, M and n are as previously defined.

Scheme III
Cyclic Poly(aryl ether) Preparation
Method A

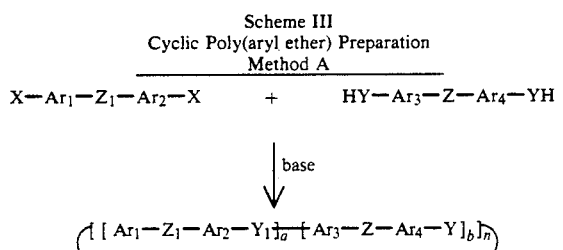

where Z, Y and n are as previously defined; $Y_1$ is divalent oxygen or divalent sulfur independently selectable from Y; $Ar_1$, $Ar_2$, $Ar_3$ and $Ar_4$ are arylene groups independently selected from the group consisting of $Ar_A$; $Z_1$ is independently selectable from the group consisting of Z; and a and b are integers of from 1 to 3. Examples of useful starting materials include 4-fluorophenyl-4-hydroxyphenyl sulfone, 4-chlorophenyl-4-hydroxyphenyl sulfone, 4-fluoro-4'-hydroxybenzophenone, 4-chloro-4'-hydroxybenzophenone, 4-fluoro-3'-hydroxybenzophenone, 4-chloro-3'-hydroxybenzophenone, 1-(4-fluorophenyl)-3-(4-hydroxyphenyl)benzene, 1-(4-fluorophenyl)-4-(4-hydroxyphenyl)benzene, 2-hydroxy-6-fluorobenzenenitrile, 2-hydroxy-4-fluorobenzenenitrile, 2-hydroxy-6-chlorobenzenenitrile, 2-hydroxy-4-chlorobenzenenitrile.

Scheme I shows the most general situation, where the electron withdrawing group could be a wide range of mono- and divalent radicals. Scheme II shows the situation where the electron withdrawing group itself contains an aromatic diradical, which would be the case for many materials of interest. In principle, $Ar_1$ and $Ar_2$ are independently selectable, although they may often be identical. Scheme III shows a situation where the cyclic oligomer contains a repeating unit derived from the dihalide that is different from the one derived from the repeating unit from the diphenol, both of which contain an aromatic diradical in the electron withdrawing group. In this case $Ar_1$-$Ar_4$ may all be the same or different in any combination, the electronegative groups Z and $Z_1$ may be the same or different, and Y and $Y_1$ may be the same or different. Method A must be used to produce this type of product where the various groups are different, rather than Method B.

The possible values for n and the distribution of molecular weights for the intermediates and products shown in these schemes can vary depending on a number of experimental variables such as concentration, temperature, starting material stoichiometry, and other factors. As used in this discussion the term oligomer refers to products in which n is from 1 to about 20. Although, technically speaking, when n is equal to 1 there is no "repeat" unit. However, when the aromatic diradical of formula (1) Ar is complex and, thus, quite long, the considerations for ring closure of the intermediate are similar to the situation where the intermediate is made up of several simple repeat units.

Ring closure is favored by low concentrations of reactants and, thereby, low concentrations of intermediates, and by high temperatures which increase the reaction rate of the ring closure reaction. Activated aryl dihalides wherein the two halide leaving groups are fluoride are preferred, since these have faster reaction rates in comparison to the corresponding chlorides or bromides.

In a particular example shown below, the aromatic group of the dihalide (F—Ar—F) and that of the diol (HO—Ar—OH) are identical.

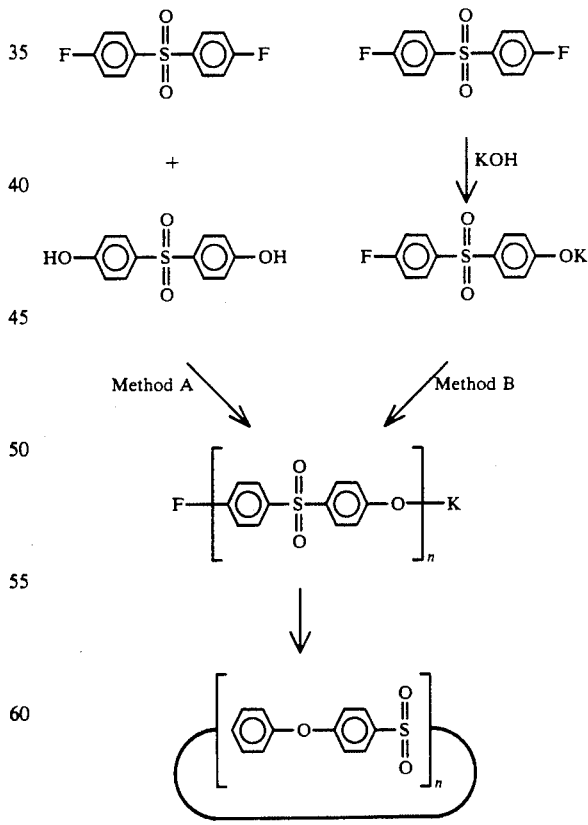

In such circumstances, Method B is preferred as cyclic structures with even and uneven numbers of repeating units (n=3, 4, 5 ...) are formed. Smaller rings (n=1 or 2) are too strained to be formed in measurable amounts in this specific example, although for some other materials where the electron withdrawing group is longer and more complex there can be significant amounts of the cyclic ether with n=1. Using Method A only cyclic structures of even numbers of repeat units starting with n=4 are formed for this specific example.

Method A is useful for preparations of cyclic poly(aryl ethers) with the repeating unit —Ar$_1$—Z—Ar$_2$—Y— where the two arylene groups are non-identical. For example, the dihalide F—C$_6$H$_4$—SO$_2$—C$_6$H$_4$—F would condense with HO—C$_6$H$_4$—C(CH$_3$)$_2$—C$_6$H$_4$—OH (Bisphenol A) to give cyclic-(C$_6$H$_4$—SO$_2$—C$_6$H$_4$—O—C$_6$H$_4$—C(CH$_3$)$_2$—C$_6$H$_4$—O)$_n$.

A third method of preparation, Method C, is to independently prepare an oligomer capped with an activated halide at one end and a phenol at the other, and react it with a base such as an alkali metal hydroxide as follows, where M is an alkali metal, e and f are integers greater than 0, and the other symbols are as indicated hereinabove:

Method C

As mentioned before, an "activated" aryl halide as used herein is defined as a halide which is attached to an aromatic ring which is substituted with an electron withdrawing group. One common electron withdrawing group is the sulfone (—SO$_2$—) group. Other examples of divalent electron withdrawing groups are —CO—, —CONH—, —CONR—, —$^+$NR$_2$—, —$^+$PR$_2$—, —$^+$SR—, —P(O)R—, —C$_6$F$_4$—, —C$_6$F$_4$C$_6$F$_4$—, —C(CF$_3$)$_2$—, —CHCH—, —N=N—, —CHNNCH—, etc., where R is C$_1$-C$_{12}$ hydrocarbyl radical, as well as electron withdrawing heterocycles such as imidazoles, oxazoles, pyrazoles, isoxazoles, and oxapyrazoles. The electron withdrawing group may be monovalent and therefore pendant to the ring rather than in the backbone. Suitable monovalent groups are —CN, —NO$_2$, —CHO, —CO$_2$R, —CO$_2$NH$_2$, —P(O)(OR)$_2$, —P(O)R$_2$, —$^+$PR$_3$, —$^+$NR$_3$, —$^+$SR$_2$, —F and —CF$_3$.

The above mentioned monovalent and divalent electron withdrawing groups possess the characteristic of being electron withdrawing primarily because of constituents of the group with relatively high electronegativity, such as F, O, N, and S. More complex electron withdrawing groups comprise the above mentioned divalent groups in various combinations with aryl groups.

The use of such starting materials, particularly combinations of activated diaryl halides and aromatic diols, to prepare high molecular weight linear polymers has been described previously. One important difference in the present invention is that the starting materials are added continuously, or in small portions at regular intervals, during the reaction, as opposed to adding them in one portion at the beginning. It is important not to add the reactants so rapidly as to produce linear products, since linear products limit the ultimate molecular weight obtainable when the desired cyclic products are polymerized. In the present invention the reactive intermediate is present in low concentrations and can cyclize at a rate faster than it can react intermolecularly to form a longer chain. The ultimate concentration of cyclic product can be high, as no ring opening occurs under these reaction conditions.

Although pure materials of a single ring size can be isolated, for the purposes of polymerization the mixtures are more desirable because they are fluid at lower temperatures. It is also possible to combine the cyclic oligomers with high molecular weight linear polymers in order to produce a mixture with relatively low melt viscosity.

Under some conditions, mixtures of cyclic poly(aryl ether) oligomers and linear poly(aryl ether) oligomers may be obtained, wherein there is at least 10 percent by weight of the cyclic oligomers.

The reaction is carried out by gradually adding solutions of the organic reactants into a reaction medium of one or more substantially inert solvents that dilute and disperse the reactants. The reaction is desirably carried out under an inert atmosphere, and a preferred atmosphere is nitrogen. The reaction medium may contain the base in solution when the addition of the organic reactants is started. Preferred bases are alkali metal hydroxides, and especially preferred are potassium hydroxide and sodium hydroxide.

High boiling dipolar aprotic solvents boiling in the range of about 50° C. to about 250° C., are suitable for preparation of solutions of the activated aryl halides, and may also be employed as the reaction medium, or as a component thereof. In the reaction medium this solvent may optionally be mixed with a solvent which forms an azeotrope with water. Preferred dipolar aprotic solvents are dimethyl sulfoxide, tetramethylsulfone, N-alkylpyrrolidinones, N,N-dialkylacetamides, N,N-dialkylformamides, tetralkyl ureas and ethers of structure R—(OCH$_2$CH$_2$—)$_n$—OR where n is 1 to 3 and R is a hydrocarbyl of 1 to 6 carbons. Especially preferred are N,N-dimethylacetamide, N-methylpyrrolidinone and dimethyl sulfoxide. For the aromatic diol and the base a polar solvent is preferred, which may be water, or a mixture of polar solvents. Suitable azeotroping solvents include hydrocarbons of from 5 to 20 carbons, optionally substituted with halogens. Preferred azeotroping solvents include chlorobenzene, xylenes, toluene benzene, hexane, heptane and octane The most preferred azeotroping solvents are toluene, benzene and hexane.

Gradual addition over times as long as ten days keep concentrations of reactants and reactive intermediates low. Suitable total reaction times range from about 1 hour to about 10 days, with the preferred reaction times being from 4 hours to 7 days. The time of addition of the organic reactants can be from about 10 to about 99 percent of the total reaction time, with a preferred range being from 20 to 90 percent of the total reaction time.

A suitable range for the concentration of all organic reactants after the addition is complete is from about 0.01 molar to about 2 molar, with a preferred concentration range being 0.01 to 0.5 molar, and the most preferred range being 0.01 to 0.2 molar.

The reaction medium is conveniently heated to a temperature at or near reflux temperature of the solvent mixture, and maintained at that temperature for the course of the reaction. A suitable range of temperatures for the reaction is from about 50° C. to about 200° C., with 50° C. to 180° C. being preferred, while from 90° C. to 180° C. is the most preferred.

PREPARATIONS OF CYCLIC POLY(ARYL ETHER) OLIGOMERS

Preparation 1

A 2 L three necked flask equipped with a thermometer, a Dean-Stark trap and condenser, and a nitrogen inlet was charged with 750 mL dimethyl sulfoxide (DMSO) and 225 mL toluene. After heating the solution to reflux (140° C. pot temperature, 127° C. distillation temperature), solutions of $FC_6H_4SO_2C_6H_4F$ in DMSO (1M, 60 mL) and aqueous KOH (2M, 60 mL) were added in approximately 5 mL portions at a rate of 1 mL/hour for the difluoride, and 2 mL/hour for the hydroxide solution. The reaction was refluxed for an additional 48 hours, and then the solvent was evaporated. The residue was washed four times with ~150 mL hot $CHCl_3$. The combined solutions were evaporated, and the light tan solid was placed in a vacuum oven at 140° C. overnight to give 7.613 g (55% yield) of a mixture of cyclic poly(ether sulfones) with $(C_6H_4-SO_2-C_6H_4-O)$ repeat units. The inherent viscosity of this mixture was 0.06 dL/g at 25.0° C. in DMAC at 0.5 g/dL, which is to be compared with 0.36 dL/g for high molecular weight linear poly(ether sulfone) (Victrex ® PES 3600G) under the same test conditions. The $CHCl_3$ insoluble residue contained additional cyclic products which were unrecovered.

Preparation 2

A 1 L three necked flask equipped with a thermometer, a Dean-Stark trap and condenser, and a nitrogen inlet was charged with 500 mL dimethyl acetamide (DMAC), diphenyl sulfone (235.9 mg) as an internal standard for analysis by liquid chromatography, and 125 mL toluene. Solutions of $F-C_6H_4-SO_2-C_6H_4-F$ (0.50M in DMAC) and $HO-C_6H_4-SO_2-C_6H_4-OH$ plus NaOH (0.50M and 1.00M respectively, in water) were prepared. After heating the solution to reflux, 4 mL of each solution was added immediately, after 21 hours, and after 50 hours of reflux. After a total of 66.4 hours, 1 mL of acetic acid was added and the solvent was evaporated to ~5 mL of a milky white suspension. The oil was boiled with 100 mL toluene which was filtered and evaporated. Analysis by liquid chromatography of the crystalline residue revealed a single peak. The infrared, $^1H$ and $^{13}C$ NMR, and mass spectra (m/e 928) are consistent with the structure $(C_6H_4-SO_2-C_6H_4-O)_4$. This substance could be polymerized to high molecular weight poly(ether sulfone), providing further confirmation for this structure. The toluene soluble portion was shown to be a mixture of cyclic oligomers of structure $(C_6H_4-SO_2-C_6H_4-O)_n$, where n is an even integer starting at 4 (4, 6, 8 ...).

Preparation 3

A 1 L three necked flask equipped with a thermometer, a Dean-Stark trap and condenser, and a nitrogen inlet was charged with 1 L dimethyl acetamide (DMAC), diphenyl sulfone (216.3 mg) as an internal standard for analysis by liquid chromatography, and 250 mL toluene. Solutions of $F-C_6H_4-CO-C_6H_4-F$ (0.50M in DMAC) and KOH (2.00M in water) were prepared. Over the course of 7 days, 28 mL of the KOH solution and 32 mL of the difluoride solution were added. After an additional day, 4 mL of acetic acid was added and the reaction was filtered to remove salt and the solvent was evaporated. The residue was boiled with 100 mL ethyl acetate which removes linear oligomers. This residue was dissolved in hot DMSO, filtered, and allowed to cool. The crystalline powder which precipitated was dried overnight at 140° C. in a vacuum oven. The $^1H$ and $^{13}C$ NMR, and mass spectra (m/e 784) are consistent with the structure $(C_6H_4-CO-C_6H_4-O)_4$.

Preparation 4

Cyclic Polyether Ketone from Bisphenol A and 1,3-Bis(4-fluorobenzoyl)benzene

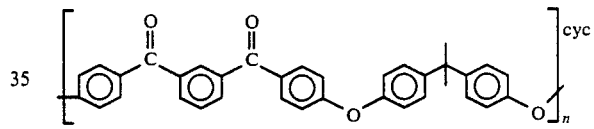

A 1 L three-necked flask equipped with a Dean-Stark trap and condenser, a thermometer, a nitrogen inlet, and magnetic stirring was charged with 450 mL DMSO (dimethyl sulfoxide) and 130 mL of toluene. After the solvents were heated to reflux (140° C. pot temperature), two solutions containing the monomers were added simultaneously using a syringe pump. The first solution was an aqueous solution of bisphenol A (0.125M) and NaOH (0.250M). The second was a solution of 1,3-bis-(4-fluorobenzoyl)benzene (0.125M) in 50/50 (v/v) DMSO/N-methylpyrrolidinone. The addition continued (rate 10 mL/hour) until 58.5 mL of both solutions were added. After an additional 18 hours of reflux (pot temperature 155°-160° C.) the reaction was allowed to cool and poured into 2 L water. The resultant mixture was extracted twice with 750 mL of 2-butanone. A layer of powder which formed at the interface of the two phases was isolated by filtration. This powder (1.321 g), a mixture of cyclics with a degree of polymerization (DP) of 1 and 2, was recrystallized from chloroform to give a single oligomer with a DP of 2 (melting point 364° C., mass spectrum: 1020 m/e). The combined organic extracts were allowed to partially evaporate, yielding an 0.906 g of solid which also consisted of a mixture of cyclics. Recrystallization from chloroform by slow solvent evaporation yielded a pure cyclic oligomer with a DP of 1 (mp 343° C., mass spectrum:510 m/e). The total yield of cyclics was 60 percent.

Preparation 6

Cyclic Poly(Aryl Ether Nitrile) from Resorcinol and 2,6-Difluorobenzenenitrile

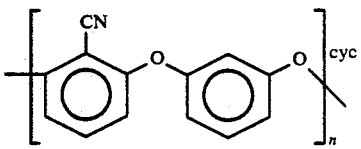

A 1 L three-necked flask equipped with a Dean-Stark trap and condenser, a thermometer, a nitrogen inlet, and magnetic stirring was charged with 400 mL N-methylpyrrolidinone, 150 mL of toluene, and 3.45 g (0.025 mole) potassium carbonate. After the solvents were heated to reflux (166° C. pot temperature), two separate 0.40M solutions of the monomers (resorcinol and 2,6-difluorobenzenenitrile) in N-methylpyrrolidinone were added simultaneously using a syringe pump. The addition continued (rate 15 mL/hour) until 50 mL of both solutions were added. During an additional hour of reflux the pot temperature was raised to 200° C. by draining toluene from the Dean-Stark trap. The reaction mixture was poured into 1 L water which was then neutralized with aqueous 1M HCl. The precipitate was filtered, washed with methanol, and treated with boiling chloroform. A pure cyclic oligomer with a DP of 4 (0.592 g, mp 397° C., mass spectrum: 836 m/e, elemental analysis found C 74.41, H 3.41, N 6.58, calculated C 74.64, H 3.37, N 6.70) precipitated from the chloroform solution on cooling. Slow evaporation of the mother liquor afforded a second crop of crystals (0.21 g) which was a pure cyclic oligomer with a DP of 3 (mp 451° C., mass spectrum: 627 m/e, elemental analysis: found C 74.71, H 3.41, N 6.75, calculated C 74.64, H 3.37, N 6.70).

Preparation 7

Preparation of Cyclic Oligomers from Hexafluorobenzene and Bisphenol A

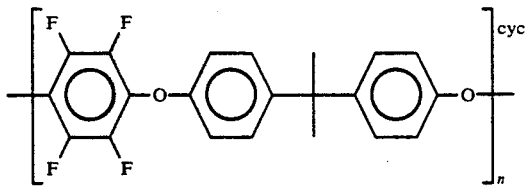

A 250 mL three-necked flask equipped with a Dean-Stark trap and condenser, a thermometer, a nitrogen inlet, and magnetic stirring was charged with 150 mL DMSO and 25 mL of benzene. After the benzene was distilled off to dehydrate the DMSO, two solutions containing the monomers were added simultaneously using a syringe pump at a pot temperature of 90° C. The first solution contained bisphenol A (5.7327 g, 1.141M) and KOH (2.35M) in DMSO/water (3/1 v/v). The second was a solution of hexafluorobenzene (1.141M) in benzene. The addition continued (rate 3.4 mL/hour) until 22 mL of both solutions were added. After an additional 15 hours of heating the reaction was allowed to cool and poured into 1 L water. The resultant mixture was extracted twice with 200 mL toluene. The combined toluene extracts were washed with 150 mL water, dried with MgSO$_4$, filtered, and evaporated. The resultant white solid was placed in a vacuum oven overnight at 120° C. to give 8.5 g crude product, which consisted of a mixture of cyclic oligomers and a high molecular weight polymer. A portion of this solid (5.2 g) was dissolved in 35 mL of acetone and precipitated with 35 mL of methanol. The suspension was filtered and the white solid was dried to give 1.32 g (25 percent yield) of a mixture of pure, low molecular weight cyclic oligomers. A single cyclic oligomer with a DP of 2 was isolated from this mixture using preparative thin layer chromatography (90/10 hexane/ethyl acetate) (mass spectrum with chemical ionization (methane): 749 m/e M+1.

Preparation 8

Preparation of Cyclic Oligomers from Hexafluorobenzene and Bisphenol A

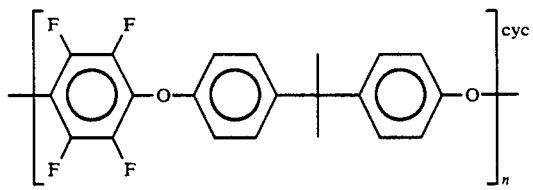

The above example was repeated using hexafluorobenzene (14.8873 g, 80.0 mmole) bisphenol A (18.2632 g, 80.0 mmole) KOH (9.5208 g, 170 mmole). The monomers were added over a 22 hour period, and heating was continued for an additional 4.5 hours. After a similar isolation procedure, 19.90 g of a mixture of cyclics and high molecular weight polymer was obtained (69 percent yield). A mixture of cyclic (6.1 g) was obtained by precipitation from acetone solution by addition of methanol as before.

Preparation 9

Cyclic Poly Ether Sulfone Synthesis

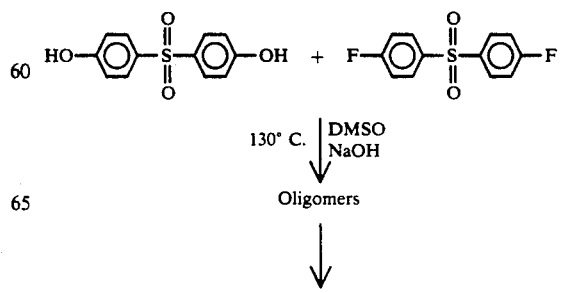

-continued

Cyclics (n = 4, 6, . . .)

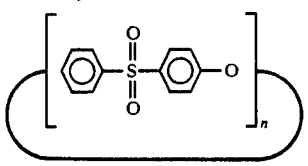

Procedure

To a 5 L, 3-necked, round-bottom flask equipped with a thermometer, air powered stirrer, Dean-Stark trap with attached water-cooled condenser and nitrogen inlet, and a syringe pump apparatus, is added 1500 mL dimethyl sulfoxide and 800 mL toluene. This is heated to reflux (130° to 135° C.) (The amount of toluene should be adjusted to maintain this reflux temperature.) At this point, 100 mL of a 0.5M solution of 4-fluorophenyl sulfone (0.05 mol; 12.71 g) and, as an internal standard, benzophenone (0.0055 mol: 0.9945 g) in DMSO is added simultaneously with 100 mL of a 0.5M aqueous solution of the sodium salt of 4,4'-sulfonyldiphenol (0 05 mol; 12.51 g of 4,4'-sulfonyldiphenol with 20 mL of 5.0N aqueous sodium hydroxide solution) at a flow rate of 20 mL/hr. Water is continually removed from the refluxing mixture by azeotropic distillation and drained from the Dean/Start trap. During this time, the temperature should be carefully monitored. Additional toluene may be added to keep reflux temperature constant.

The flask contents are refluxed for 20 more hours. At the end of this time, a sample is analyzed by HPLC (using a ODS Hypersil, 5 $\mu$m, 100×2.1 mm column). The yields of n=4, 6, 8, and 10 cyclics are calculated on the basis of the internal standard. The yields of cyclic PES are: 21 percent of the n=4 isomer, 9 percent of the n=6 isomer, 4 percent of the n=8 isomer, and 5 percent of the n=10 isomer. The total yield of cyclic PES is 39 percent. The high molecular weight polymer accounts for 17 percent yield. The mixture is cooled and 5 mL of acetic anhydride is added.

The solution is then evaporated to approximately 150 mL. The residue is precipitated in water and the solid is washed with methanol. This solid is dried in air for several hours, then in a vacuum oven at 80° C. for several more hours.

The crude product is added to 100 mL dimethylformamide to dissolve high molecular weight polymer and low molecular weight linear oligomers. The insoluble white powder remaining is isolated and amounts to 3.47 g (15.0 percent yield). HPLC analysis shows this is the 4-membered cyclic ether sulfone and a trace of 6-membered cyclic. The high molecular weight polymer is absent.

The mother liquor is evaporated to dryness and the residue is subjected to the isolation procedure again to recover additional 4-membered cyclic oligomer (1.07 g; 4.6 percent yield). The total isolated yield of 4-membered cyclic is thus 4.54 g (19.6 percent yield).

Polymerization of Cyclic Aryl Ether Oligomers

Although aryl ethers and aryl ether polymers are well known for thermal stability and chemical resistance, the Applicants have discovered a catalyst which reversibly cleaves the cyclic ethers, ultimately producing a polymer. This process is shown for some specific examples in Scheme 1.

Scheme 1
Polymerization Mechanism

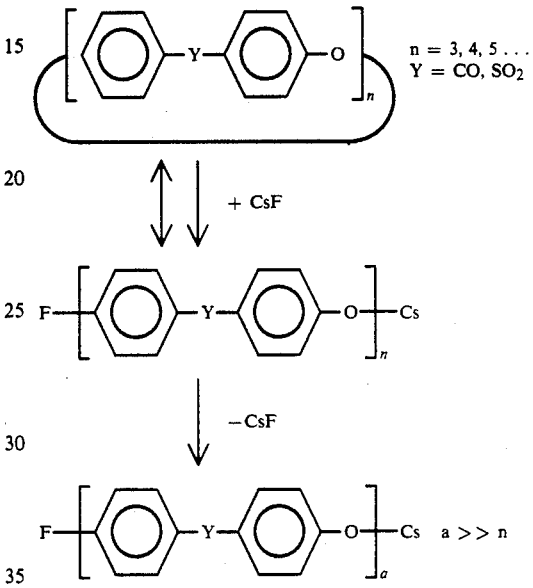

In the case where the 'Y' moiety is sulfone ($SO_2$), it is observed that the mixture of cyclic starting materials is transformed from a free flowing liquid to an immobile, clear polymer on heating to 300° C. in the presence of CsF catalyst. The inherent viscosities determined in dimethyl acetamide solution of the starting material and product are 0.04 to 0.06 dL/g and 0.34 to 0.50 dL/g, respectively. Analysis of the product by differential calorimetry revealed a 225° C. glass transition temperature (10° C./min, inflection point). For comparison, a commercially available polymer of a similar basic structure (Victrex ® PES 3600G from Imperial Chem. Ind.) has an inherent viscosity of 0.36 dL/g and an identical glass transition temperature.

This method is applicable to the preparation of a wide variety of aryl ether or aryl thioether containing polymers. High molecular weight linear polymers which contain a phenylene ether moiety in the backbone in which the phenylene group is also substituted with an electron withdrawing group may be prepared using this technology.

Ring opening catalysts for the ring opening polymerization of these cyclic oligomers are salts of the type $M_cB_d$ where M is a monovalent or divalent metal, $+NR_4$ or $+PR_4$ where R is a hydrocarbyl radical of 1-12 carbon atoms, imidazole, oxazole, pyrazole, isoxazole or oxapyrazole, B is a halide, carbonate, hydrogen carbonate, aryl or alkyl oxide, cyanide, nitrate, nitrite, hydroxide, phosphate, or aryl or alkyl carboxylate, and c and d are integers which satisfy valency requirements. Alkali metal halides are preferred catalysts with cesium fluoride being a highly preferred catalyst.

A mixture of compounds which react thermally under conditions suitable otherwise for the polymerization process may be used to produce the catalyst in situ. For example, a mixture of $CsOC_6H_4SO_2C_6H_4OCs$ and $FC_6H_4SO_2C_6H_4F$ reacts to release finely dispersed CsF and poly(ether sulfone). Since thorough dispersal of the catalyst throughout the polymerization mixture is highly desirable this is a preferred method of introducing the catalyst. In situ production of the catalyst is preferred also because, when finely dispersed in this manner, catalyst efficiency is increased in any given local area, and less catalyst is required overall.

Preferred catalyst concentrations range from about 0.1 percent to about 10 percent by weight of the polymerizable mixture. A range of about 0.5%–5% by weight is more preferred, with the most preferred range of concentrations being from about 0.5%–2.5% by weight of the polymerizable mixture.

These polymerizations preferably are performed neat, without any solvent. However, in some cases there is an advantage to the use of solvent where it aids in the dissolution of the ring opening polymerization catalyst. Useful solvents include high boiling polar solvents, especially diphenyl sulfone, benzophenone, dimethyl sulfoxide, dimethyl acetamide, N-methylpyrrolidinone, N-cyclohexylpyrrolidinone, with diphenyl sulfone being highly preferred.

The temperatures used for ring opening polymerizations of this invention range from about 250° C. to about 450° C., with the range from 275° C. to 400° C. being preferred, and especially preferred being the range from 275° C. to 375° C.

The product of the above described polymerization process is an article. In another embodiment of the present invention a polymerizable composite composition which contains a reinforcing material and at least one cyclic poly(aryl ether) oligomer as described above is employed in a similar process. The result in this case is a composite. As discussed earlier the processing advantages due to the low melt viscosities of the oligomers or solutions thereof result in superior properties for the finished article and the composite.

The following examples illustrate the present invention and in no way are intended to limit the scope of the present invention.

EXAMPLE 1

A suspension of 302 mg cyclic poly(ether sulfone) oligomers ($\eta$inh 0.06 dL/g at 0.5 g/dL in DMAC at 25.0° C.) plus 12 mg CsF in 0.5 mL MeOH was prepared in a 5 mL flask. The solvent was removed under vacuum using a short path still, and then the flask was immersed in a 300° C. molten salt bath while still under vacuum. After 20 minutes the flask was vented to nitrogen, and heating was continued for an additional 105 minutes. A clear, light brown, flexible film was removed from the flask. Analysis of this film ($\eta$inh 0.34 dL/g at 0.5 g/dL in DMAC at 25.0° C.) indicated that it was poly(ether sulfone). For comparison the $\eta$inh of commercial poly(ether sulfone) (Victrex® PES 3600G) has an $\eta$inh of 0.36 dL/g under identical conditions. A glass transition temperature of 225° C. (inflection point, 10° C./min) was measured by differential scanning calorimetry, which is identical to that observed for the commercial polymer.

EXAMPLE 2

A 10 mL round-bottom flask was charged with cyclic $(C_6H_4-SO_2-C_6H_4-O)_4$ (158.3 mg), diphenyl sulfone (613.1 mg), and 4 mL chlorobenzene. A short path still was attached, and the chlorobenzene was distilled off in a nitrogen atmosphere to remove water. The catalyst was then added (24.1 mg CsF) and the flask was immersed in a 260° C. molten salt bath. The bath temperature was gradually raised to 300° C. during a 215 minute heating period. The product was washed out of the flask with $Cl_2CHCHCl_2$. This solution was evaporated and the diphenyl sulfone was removed by bulb-to-bulb distillation at 200° C. (0.1 mm Hg). The $\eta$inh of the resultant polymer was 0.50 dL/g at 0.5 g/dL in $Cl_2CHCHCl_2$ at 25.0° C.

EXAMPLE 3

Polymerization of Cyclic Poly(Ether Ketone)

A quantity of the cyclic poly(ether ketone) oligomers shown in preparation 4 (15 mg) were dissolved in 1 mL chloroform and treated with sufficient CsF solution (1 mg/mL) to give a 0.5 to 1.0 percent (w/w) suspension. The solvents were then evaporated and the solid was heated to temperatures ranging from 300° to 365° C. for about 1 hour. The resultant polymer had a glass transition temperature of 151° C., comparable to that reported (153° C.) for the high molecular weight linear polymer.

EXAMPLE 4

Eight plies of carbon fiber fabric (8-harness satin weave, AS 4 fiber) are placed in the lower half of a two-part steel mold. To his mold is added evenly a mixture comprising 99.5 parts by weight of phenylene-ether-sulfone cyclics and 0.5 part by weight of cesium fluoride. The quantity of this mixture is such that it will comprise 25 to 35 percent by weight of the resulting composite panel. The top half of the steel mold is joined with the lower half and the closed mold is evacuated. Heat and pressure are then applied to the mold to melt the cyclic oligomers, compact the fiber-resin mixture and to initiate their polymerization. The preferred temperature range is from 200°–300° C. and the projected time of polymerization is from to 5 hours. After the mold cools to room temperature it is opened and the composite panel is removed.

EXAMPLE 5

A mixture of the cyclic oligomers and cesium fluoride as described in Example 4 is intimately blended with an equal amount of chopped quartz fibers. The blend is then placed in the mold described above and polymerized in the same manner to yield a quartz fiber reinforced plastic panel.

What is claimed is:

1. A process for the preparation of poly(aryl ethers) which comprises contacting a polymerizable composition comprising at least one cyclic poly(aryl ether) oligomer represented by the formula:

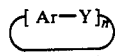

where each Y is divalent oxygen or divalent sulfur, each Ar is an aromatic diradical which has at least one electron withdrawing group attached to the aromatic ring other than Y, and n is an integer greater than 1, with a ring opening polymerization catalyst at a temperature from 250° C. to 450° C.

2. The process of claim 1 wherein at least one aromatic ring of the aromatic diradical Ar has attached to it 1-4 monovalent electron withdrawing groups.

3. The process of claim 2 wherein said monovalent electron withdrawing groups are independently selected from —CN, —NO$_2$, —CHO, —CO$_2$R, —CO$_2$NH$_2$, —F, —CF$_3$, —P(O)(OR)$_2$, —P(O)R$_2$, —+PR$_3$, —+NR$_3$, —+SR$_2$, where R is a hydrocarbyl radical of 1-12 carbon atoms, imidazole, oxazole, pyrazole, isoxazole or oxapyrazole.

4. The process of claim 1 wherein at least two aromatic rings of the aromatic diradical are attached by a divalent electron withdrawing group which is in the backbone of the oligomer.

5. The process of claim 4 wherein the divalent electron withdrawing group comprises an electronegative group Z which is —SO$_2$—, —CO—, —CONH—, —CONR—, —+NR$_2$—, —+PR$_2$—, —+SR—, —P(O)R—, —C$_6$F$_4$—, —C$_6$F$_4$C$_6$F$_4$—, —C(CF$_3$)$_2$—, —CHCH—, —N=N—, —CHNNCH—, where R is a hydrocarbyl radical of 1-12 carbon atoms, imidazole, oxazole, pyrazole, isoxazole or oxapyrazole, said oligomer represented by the formula

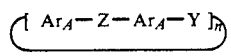

where Y and n are as previously defined and each Ar$_A$ is an arylene group containing at least one aromatic ring.

6. A process according to claim 5 wherein Ar$_A$ is selected from the group consisting of:

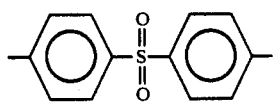

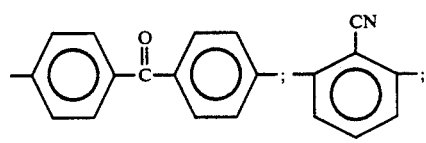

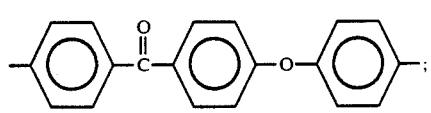

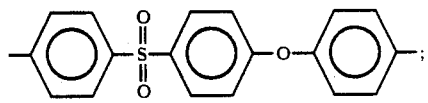

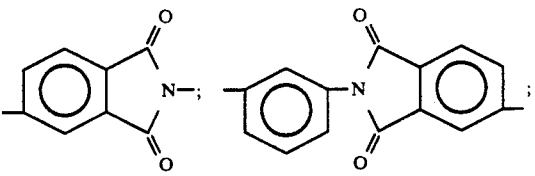

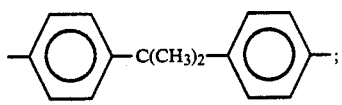

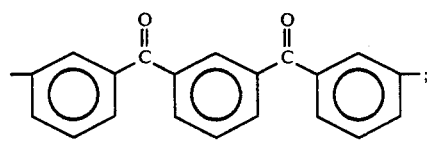

and

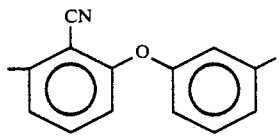

7. A process of claim 4 wherein the aromatic diradical additionally contains one or more linking groups, L, in the backbone of the oligomer where L is selected from the group consisting of:

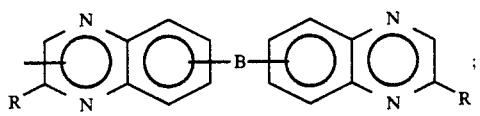

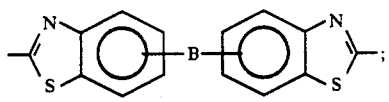

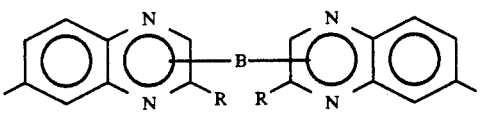

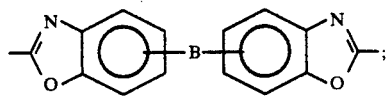

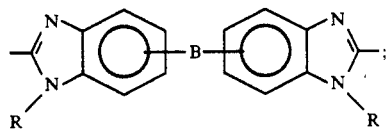

-continued

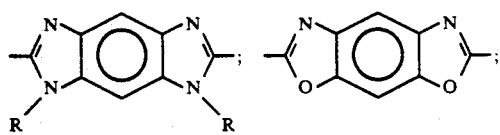

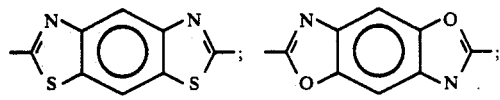

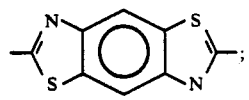

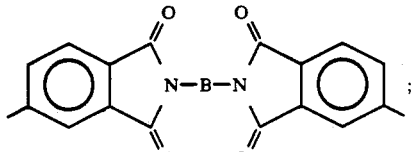

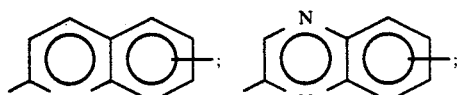

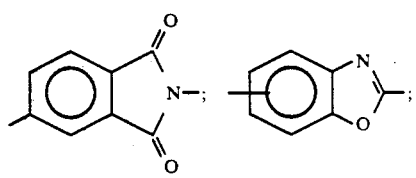

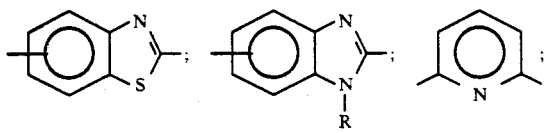

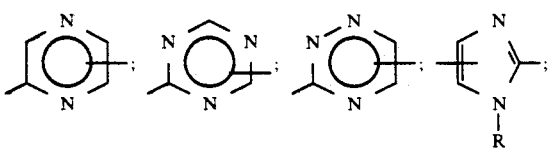

-continued

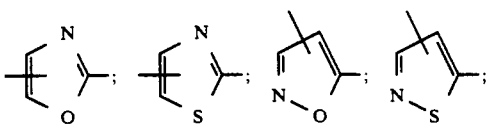

and

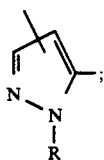

where:
R is a $C_1$ to $C_{12}$ hydrocarbyl radical;
each of the heterocycles may be additionally substituted with one or more groups selected from: $C_1$ to $C_{12}$ hydrocarbyl radicals, halogens, $C_1$ to $C_{12}$ alkoxy or aryloxy radicals, cyano, nitro, alkyolcarbonyl, formyl, alkoxycarbonyl, aryloxycarbonyl, or arylsulfonyl radicals and;
B is in each occurrance a direct bond, —O—, —S—, —SO$_2$—, a carbonyl, a phosphinyl, a phosphine oxidyl, a tertiary amindiyl, or a $C_1$ to $C_{24}$ hydrocarbylene radical optionally substituted with one or more groups selected from halogens, $C_1$ to $C_{12}$ alkoxy or aryloxy radicals, cyano, nitro, alkylcarbonyl, formyl, alkoxycarbonyl, aryloxycarbonyl, arylsulfonyl, or carbonylarylcarbonyl radicals.

8. The process of claim 7 wherein the cyclic poly(aryl ether) oligomer is represented by the formula

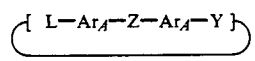

where Y, n, Z, Ar$_4$, and L are as previously defined.

9. The process of claim 1 wherein the polymerizable composition comprises a mixture of cyclic poly(aryl ether) oligomers as described in claim 1.

10. The process of claim 1 wherein the cyclic poly(aryl ether) oligomers is represented by:

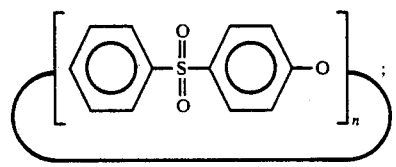

I

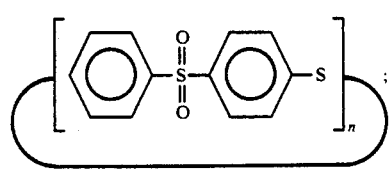

II

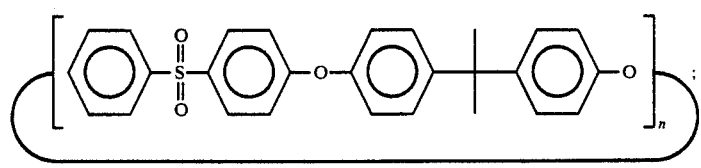
III
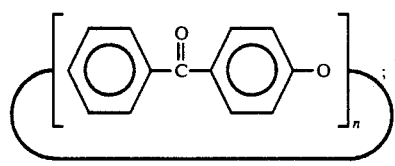
IV
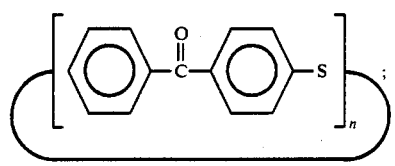
V
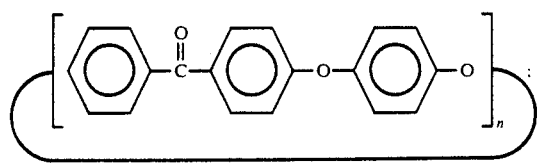
VI
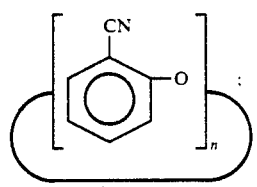
VII
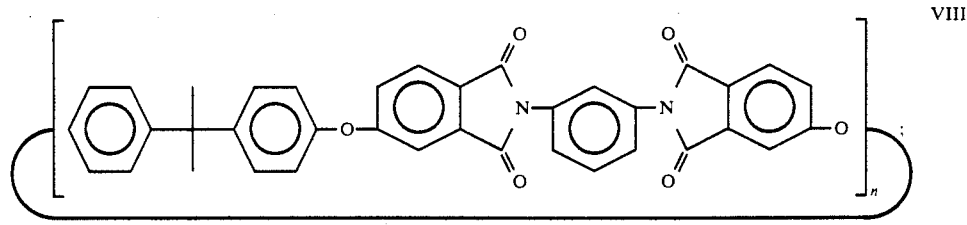
VIII
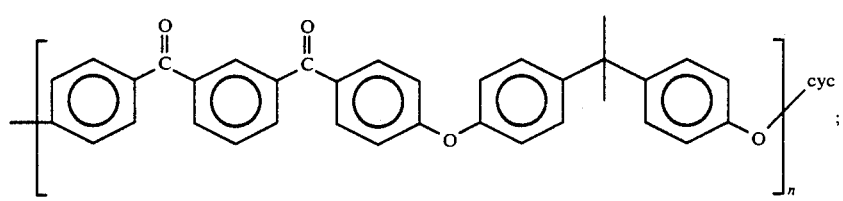
IX
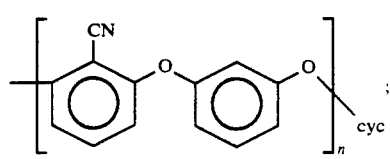
X
or

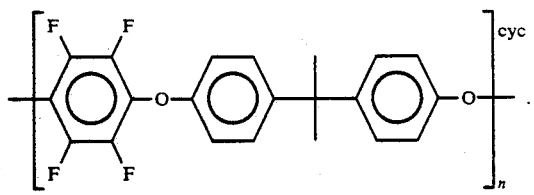

11. The process of claim 10 wherein the cyclic poly(aryl ether) oligomer is represented by

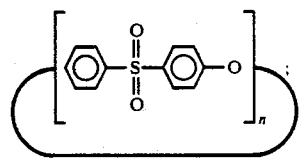

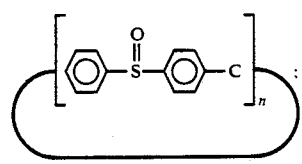

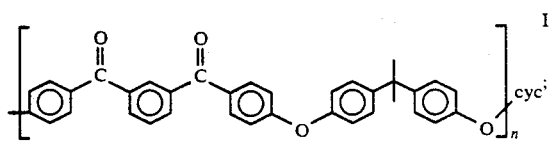

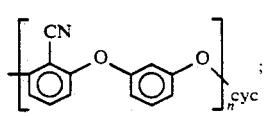

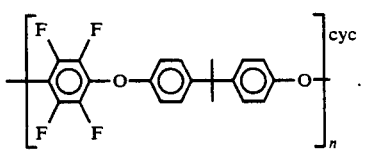

or

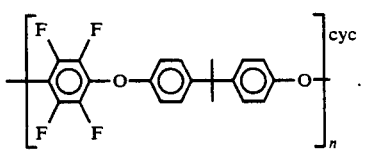

12. The process of claim 1 wherein the cyclic poly(aryl ether) oligomer is represented by the formula

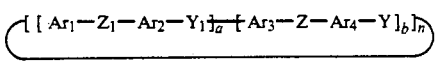

where Z, Y, and n are as previously defined; $Y_1$ is divalent oxygen or divalent sulfur; $Ar_1$, $Ar_2$, $Ar_3$ and $Ar_4$ are arylene groups; $Z_1$ is independently selected from the group consisting of Z; and a and b are integers of from 1 to 3.

13. The process of claim 12 wherein the cyclic poly(aryl ether) oligomer is represented by the formula:

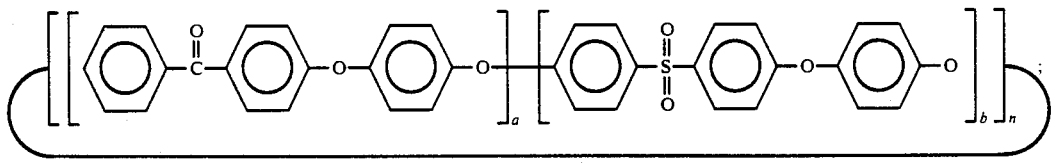

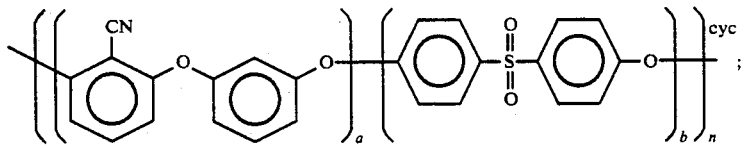

or

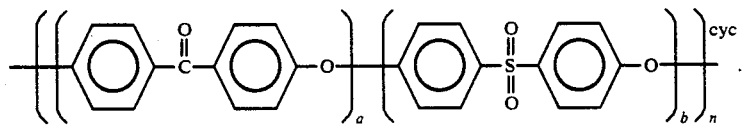

14. The process of claim 9 wherein the cyclic poly(aryl ether) oligomer of said mixture are represented by the formula:

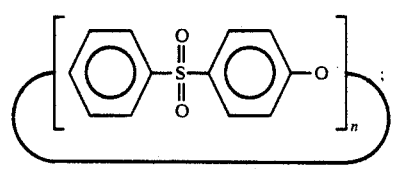 I
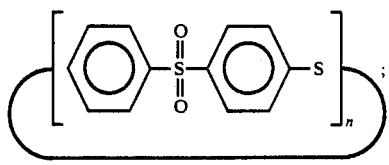 II
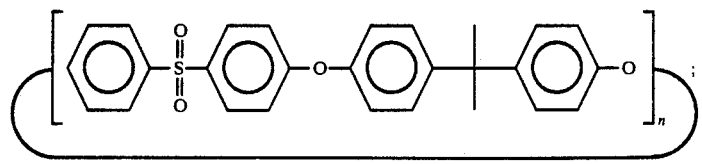 III
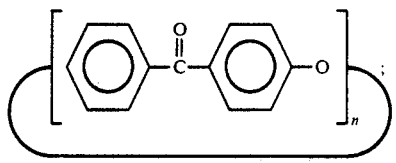 IV
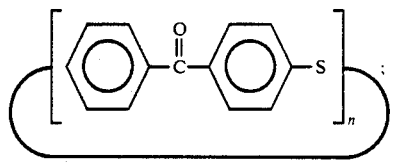 V
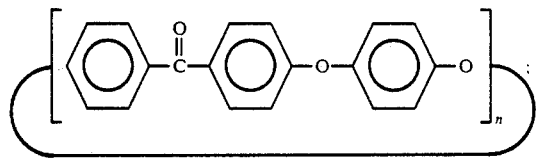 VI
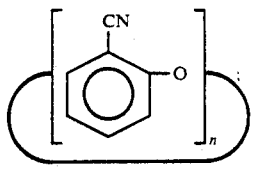 VII
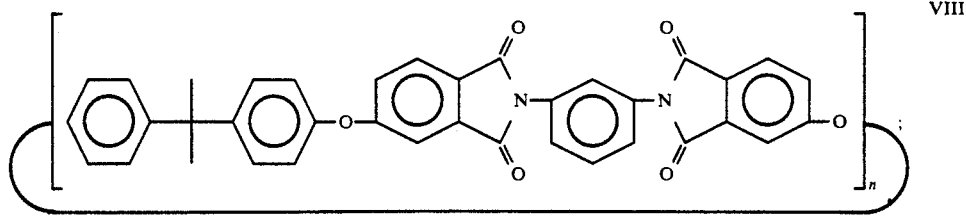 VIII
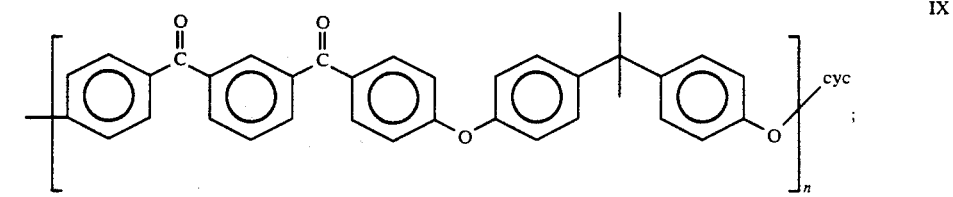 IX

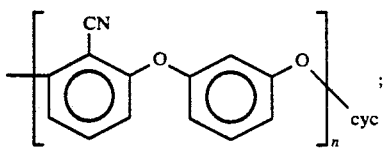

or

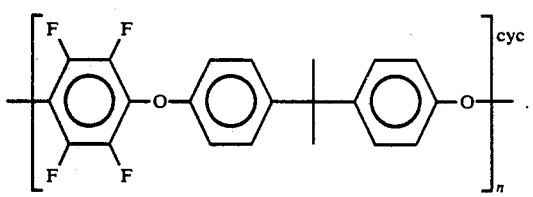

15. The process of claim 14 wherein the cyclic poly(aryl ether) oligomers of said mixture are represented by one or more of formulas I, IV, IX, X and XI.

16. The process of claim 9 wherein the cyclic poly(aryl ether) oligomers of said mixture are represented by the formula

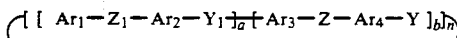

where Z, Y and n are as previously defined; $Y_1$ is divalent oxygen or divalent sulfur independently selectable from Y; $Ar_1$, $Ar_2$, $Ar_3$ and $Ar_4$ are arylene groups independently selected from the group consisting of $Ar_A$; $Z_1$ is independently selectable from the group consisting of Z; and a and b are integers of from 1 to 3.

17. The process of claim 1 wherein the polymerizable composition comprises a mixture of
(a) at least 10 percent of one or more cyclic poly(aryl ether) oligomers represented by the formula

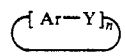

and
(b) up to 90 percent of one or more linear poly(aryl ether) polymers wherein the repeating unit is

where Ar, Y and n are as previously defined and m is an integer greater than 20.

18. The process according to claim 1 wherein the polymerizable composition is prepared by admixing at least one cyclic poly(aryl ether) oligomer and a ring opening polymerization catalyst in an inert diluent and then removing said diluent therefrom.

19. The process of claim 18 wherein the inert diluent is a high boiling polar liquid.

20. The process of claim 19 wherein the high boiling polar liquid is diphenyl sulfone, benzophenone, dimethyl sulfoxide, dimethyl acetamide, N-methylpyrrolidinone or N-cyclohexylpyrrolidinone.

21. The process of claim 1 wherein the ring opening polymerization catalyst is a salt represented by the formula $M_cB_d$, where M is a monovalent metal ion, a divalent metal ion, $^+NR_4$ or $^+PR_4$, where R is a hydrocarbyl radical of 1-12 carbon atoms, imidazole, oxazole, pyrazole, isoxazole or oxapyrazole, B is a halide, carbonate, hydrogen carbonate, aryl or alkyl oxide, cyanide, nitrate, nitrite, hydroxide, phosphate, or aryl or alkyl carboxylate, and c and d are integers which satisfy valency requirements.

22. The process of claim 21 wherein the ring opening polymerization catalyst is cesium fluoride.

23. The process of claim 1 wherein the ring opening polymerization catalyst is produced in situ.

24. The process of claim 23 wherein the in situ produced ring opening polymerization catalyst is derived from the reaction of a dihalogenobenzenoid compound and a metal salt of a bisphenol compound.

25. The process of claim 24 wherein the in situ produced ring opening polymerization catalyst is derived from a mixture of $CsOC_6H_4SO_2C_6H_4OCs$ and $FC_6H_4SO_2C_6H_4F$.

26. The process of claim 1 wherein the ring opening polymerization catalyst comprises from about 0.1 percent to about 10 percent by weight of the polymerizable composition.

27. The process of claim 26 wherein the ring opening polymerization catalyst comprises from about 0.5 percent to about 5 percent by weight of the polymerizable composition.

28. The process of claim 27 wherein the ring opening polymerization catalyst comprises from about 0.5 percent to about 2.5 percent by weight of the polymerizable composition.

29. The process of claim 1 wherein the temperature is from about 275° C. to about 400° C.

30. The process of claim 29 wherein the temperature is from about 275° C. to about 375° C.

31. A process for the preparation of a composite which comprises contacting a polymerizable composite composition comprising a reinforcing material and at least one cyclic poly(aryl ether) oligomer represented by the formula:

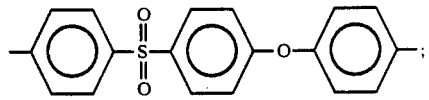

where each Y is a divalent oxygen or divalent sulfur, each Ar is an aromatic diradical which comprises one or more $C_6$ to $C_{20}$ arylene groups and has at least one electron withdrawing group attached to an aromatic ring, and n is an integer from 1 to about 20 with the proviso that for integer values of n equal to 1 to 2 all linkages between independent aromatic rings comprise at least one atom, with a ring opening polymerization catalyst at a temperature from 250° C. to 450° C.

32. The process of claim 31 wherein at least one aromatic ring of the aromatic diradical Ar has attached to it 1-4 monovalent electron withdrawing groups.

33. The process of claim 32 wherein said monovalent electron withdrawing groups are independently selected from —CN, —NO$_2$, —CHO, —CO$_2$R, —CO$_2$NH$_2$, —F, —CF$_3$, —P(O)(OR)$_2$, —P(O)R$_2$, —$^+$PR$_3$, —$^+$NR$_3$, —$^+$SR$_2$, where R is a hydrocarbyl radical of 1-12 carbon atoms, imidazole, oxazole, pyrazole, isoxazole or oxapyrazole.

34. The process of claim 31 wherein two aromatic rings of the aromatic diradical are connected by a divalent electron withdrawing group which is in the backbone of the oligomer.

35. The process of claim 34 wherein the divalent electron withdrawing group comprises an electronegative group Z which is —SO$_2$—, —CO—, —CONH—, —CONR—, —$^+$NR$_2$—, —$^+$PR$_2$—, —$^+$SR—, —P(O)R—, —C$_6$F$_4$—, —C$_6$F$_4$C$_6$F$_4$—, —C(CF$_3$)$_2$—, —CHCH—, —N=N—, —CHNNCH—, where R is a hydrocarbyl radical of 1-12 carbon atoms, imidazole, oxazole, pyrazole, isoxazole or oxapyrazole, said oligomer represented by the formula

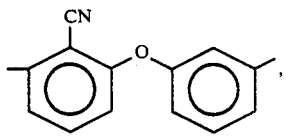

where Y and n are as previously defined and each Ar$_A$ is an arylene group containing at least one aromatic ring.

36. The process of claim 35 wherein Ar$_A$ is selected from the group consisting of:

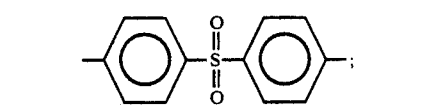

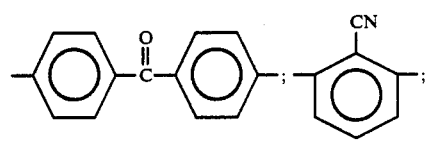

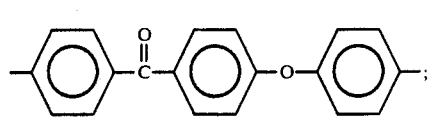

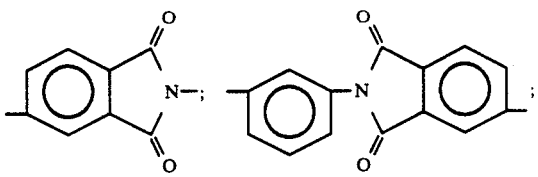

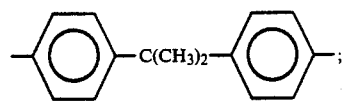

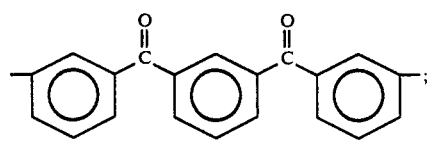

and

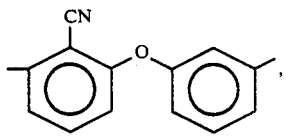

where Y, Ar, Z and n are as previously defined, and Ar$_1$ is an aromatic diradical which may be the same as or different from Ar.

37. The process of claim 34 wherein the aromatic diradical additionally contains one or more linking groups, L, in the backbone of the oligomer, where L is selected from the group consisting of:

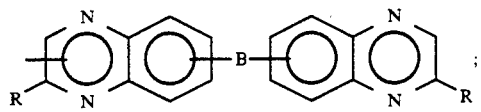

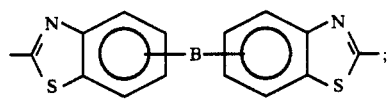

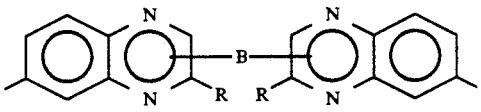

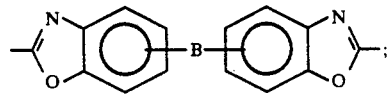

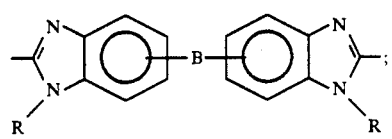

-continued

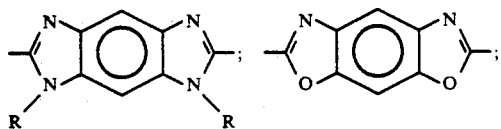
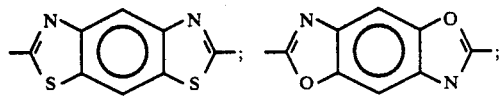
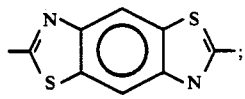
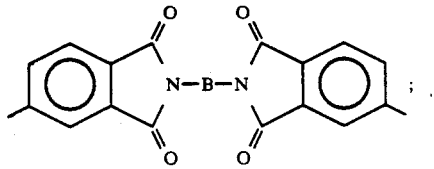
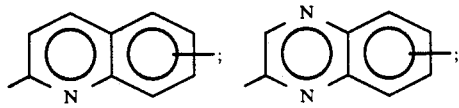
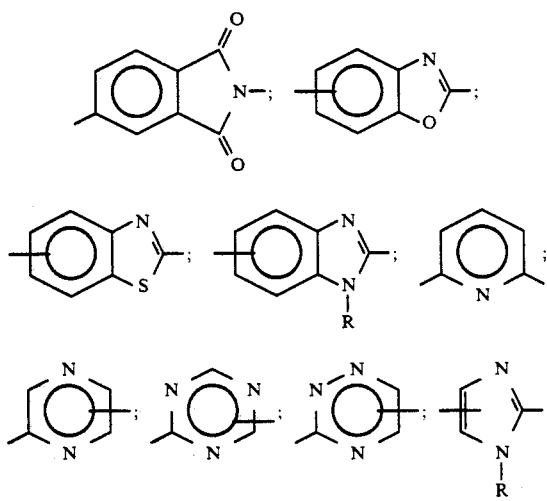
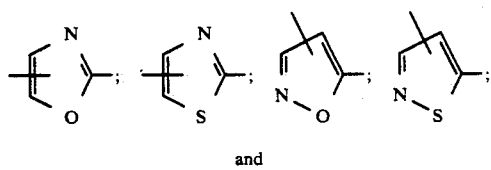

and

-continued

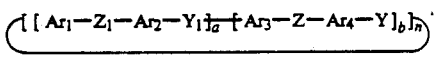

where:
R is a $C_1$ to $C_{12}$ hydrocarbyl radical;
each of the heterocycles may be additionally substituted with one or more groups selected from $C_1$ to $C_{12}$ hydrocarbyl radicals, halogens, $C_1$ to $C_{12}$ alkoxy or aryloxy radicals, cyano, nitro, alkylcarbonyl, formyl, alkoxycarbonyl, aryloxycarbonyl, or arylsulfonyl radicals; and
B is in each occurrence a direct bond, —O—, —S—, —SO$_2$—, a carbonyl, a phosphinyl, a phosphine oxidyl, a tertiary amindiyl, or a $C_1$ to $C_{24}$ hydrocarbylene radical optionally substituted with one or more groups selected from halogens, $C_1$ to $C_{12}$ alkoxy or aryloxy radicals, cyano, nitro, alkylcarbonyl, formyl, alkoxycarbonyl or aryloxycarbonyl, arylsulfonyl, or carbonylarylcarbonyl radicals.

38. The process of claim 31 wherein the cyclic poly(aryl ether) oligomer is represented by the formula $$\left( \left[ Ar_1 - Z_1 - Ar_2 - Y_1 \right]_a \left[ Ar_3 - Z - Ar_4 - Y \right]_b \right)_n$$

where Z, Y and n are as previously defined; $Y_1$ is divalent oxygen or divalent sulfur independently selectable from Y; $Ar_1$, $Ar_2$, $Ar_3$ and $Ar_4$ are arylene groups independently selected from the group consisting of $Ar_A$; $Z_1$ is independently selectable from the group consisting of Z; and a and b are integers of from 1 to 3.

39. The process of claim 37 wherein the cyclic poly(aryl ether) oligomer is represented by the formula $$\left( L - Ar_A - Z - Ar_A - Y \right)_n$$

where Y, n, Z, $Ar_A$, and L are as previously defined.

40. The process of claim 31 wherein the polymerizable composite composition comprises a mixture of cyclic poly(aryl ether) oligomers as described in claim 33.

41. The process of claim 31 wherein the cyclic poly(aryl ether) oligomer is represented by the formula:

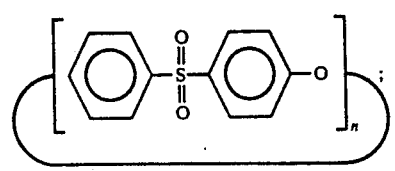

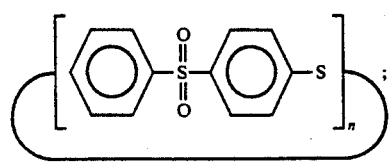 II
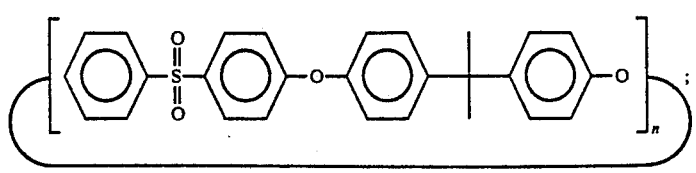 III
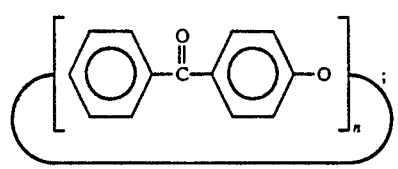 IV
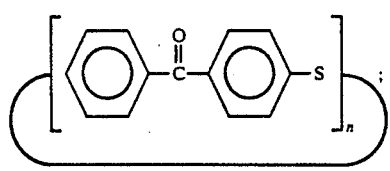 V
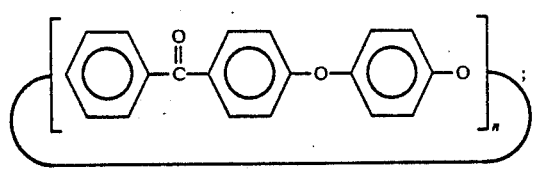 VI
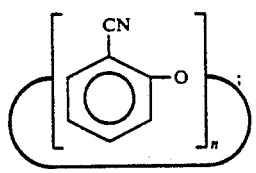 VII
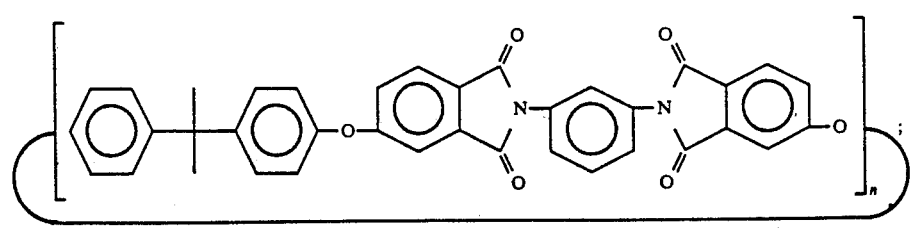 VIII
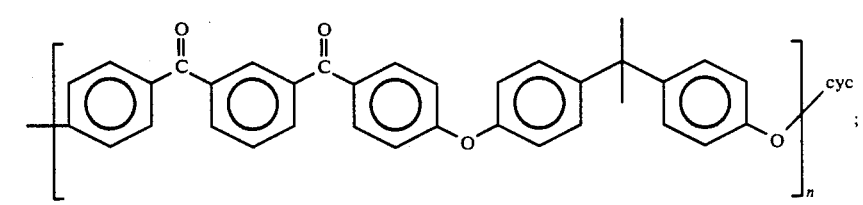 IX
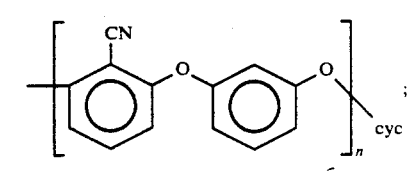 X
or

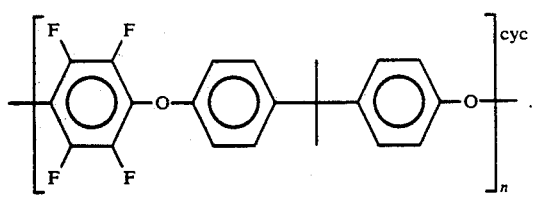
XI
42. The process of claim 41 wherein the cyclic poly(aryl ether) oligomer is represented by the formula:
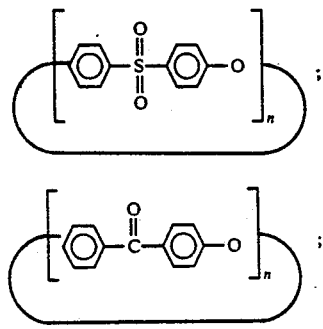
IX
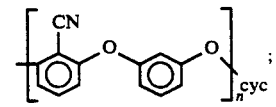
X
or
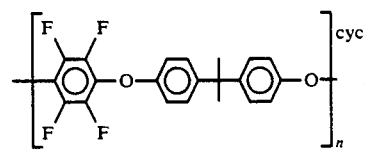
XI
43. The process of claim 38 wherein the cyclic poly(aryl ether) oligomer is represented by the formula:
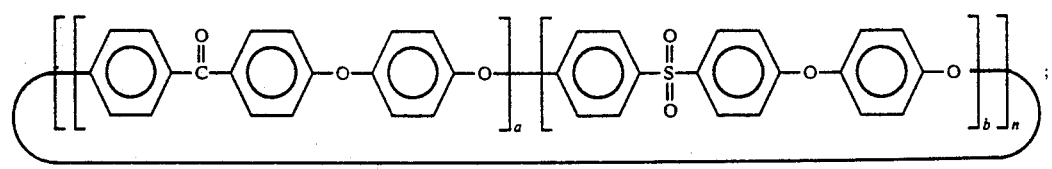
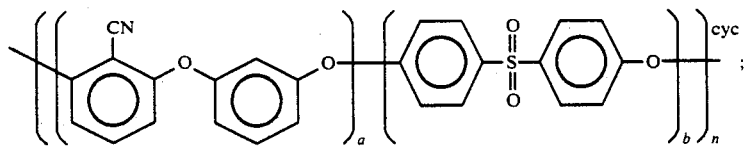
or
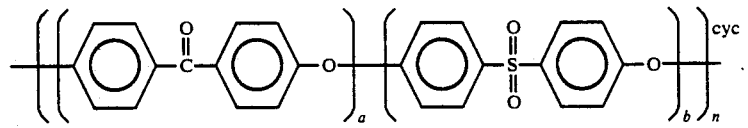
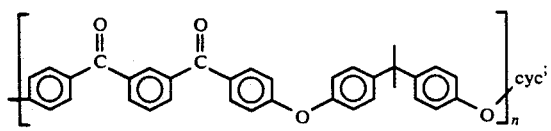
44. The process of claim 40 wherein the cyclic poly(aryl ether) oligomers of said mixture are represented by the formula:
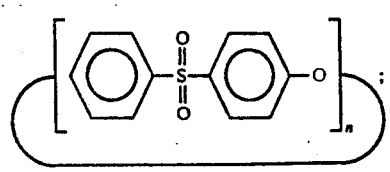
I -continued
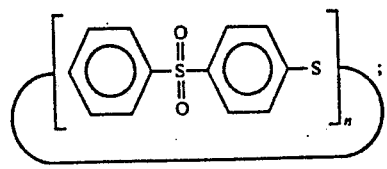 II
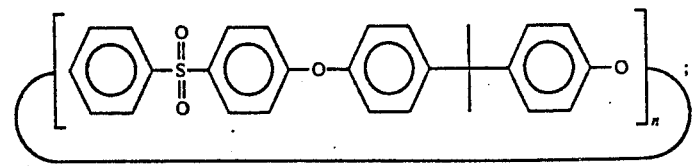 III
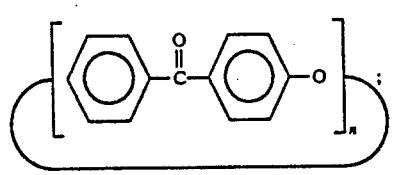 IV
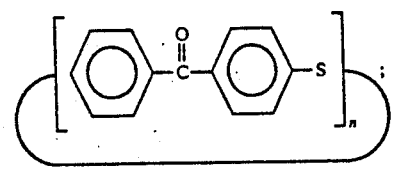 V
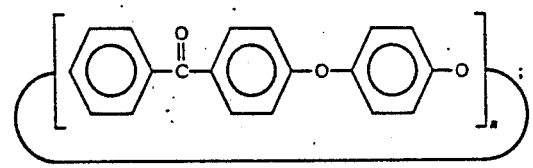 VI
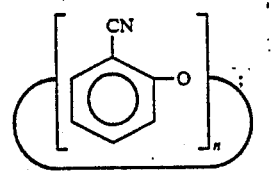 VII
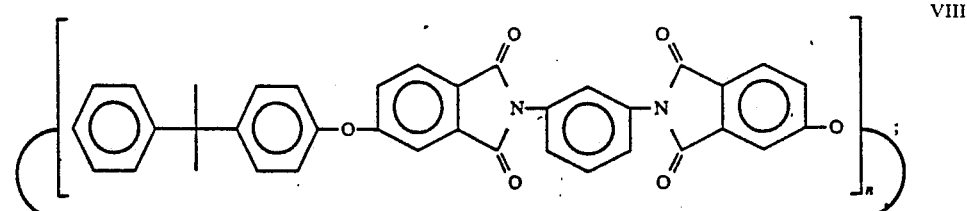 VIII
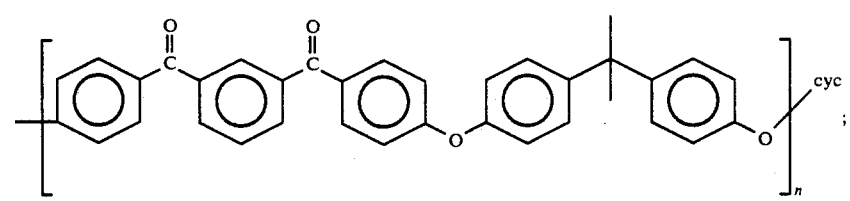 IX
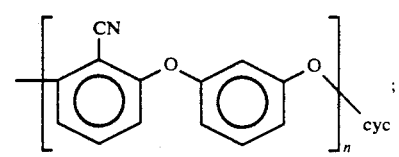 X
or

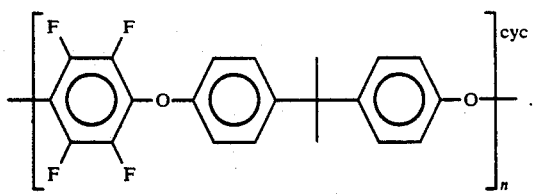

XI

45. The process of claim 40 wherein the cyclic poly(aryl ether) oligomer is represented by the formula:

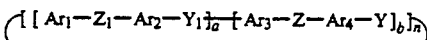

where Z, Y, and n are as previously defined; $Y_1$ is divalent oxygen or divalent sulfur; $Ar_1$, $Ar_2$, $Ar_3$ and $Ar_4$ are arylene groups; $Z_1$ is independently selected from the group consisting of Z; and a and b are integers of from 1 to 3.

46. The process of claim 14 wherein the cyclic poly(aryl ether) oligomers of said mixture are represented by one or more of formulas I, IV, IX, X or XI.

47. The process of claim 31 wherein the polymerizable composite composition comprises
(a) at least 10 of one or more cyclic poly(aryl ether) oligomers represented by the formula

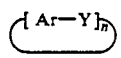

and
(b) up to 90 percent of one or more linear poly(aryl ether) polymers wherein the repeating unit is

where Ar, Y and n are as previously defined and m is an integer greater than 20.

48. The process according to claim 31 wherein the polymerizable composite composition is prepared by admixing at least one cyclic poly(aryl ether) oligomer, a ring opening polymerization catalyst and at least one reinforcing material in an inert diluent and then removing said diluent therefrom.

49. The process of claim 48 wherein the diluent is a high boiling polar liquid.

50. The process of claim 49 wherein the high boiling polar liquid is diphenyl sulfone, benzophenone, dimethyl sulfoxide, dimethyl acetamide, N-methylpyrrolidinone or N-cyclohexylpyrrolidinone.

51. The process of claim 31 wherein the ring opening polymerization catalyst is a salt represented by the formula $M_cB_d$, where M is a monovalent metal ion, a divalent metal ion, $+NR_4$ or $+PR_4$, where R is a hydrocarbyl radical of 1-12 carbon atoms, imidazole, oxazole, pyrazole, isoxazole or oxapyrazole, B is a halide, carbonate, hydrogen carbonate, aryl or alkyl oxide, cyanide, nitrate, nitrite, hydroxide, phosphate, or aryl or alkyl carboxylate, and c and d are integers which satisfy valency requirements.

52. The process of claim 51 wherein the ring opening polymerization catalyst is cesium fluoride.

53. The process of claim 31 wherein the ring opening polymerization catalyst is produced in situ.

54. The process of claim 53 wherein the in situ produced ring opening polymerization catalyst is derived from the thermal reaction of a dihalogenobenzenoid compound and a metal salt of a bisphenol compound.

55. The process of claim 54 wherein the in situ produced ring opening polymerization catalyst is derived from a mixture of $CsOC_6H_4SO_2C_6H_4OCs$ and $FC_6H_4SO_2C_6H_4F$.

56. The process of claim 31 wherein the ring opening polymerization catalyst comprises from about 0.1 percent to about 10 percent by weight of the polymerizable composition.

57. The process of claim 56 wherein the ring opening polymerization catalyst comprises from about 0.5 percent to about 5 percent by weight of the polymerizable composition.

58. The process of claim 57 wherein the ring opening polymerization catalyst comprises from about 0.5 percent to about 2.5 percent by weight of the polymerizable composition.

59. The process of claim 31 wherein the temperature is from about 275° C. to about 400° C.

60. The process of claim 59 wherein the temperature is from about 275° C. to about 375° C.

61. The process of claim 31 wherein the reinforcing material is a fiber of glass, carbon or a mixture thereof.

62. An article made by the process of claim 1.

63. A composite made by the process of claim 31.

* * * * *